United States Patent
Li et al.

(10) Patent No.: US 11,771,673 B2
(45) Date of Patent: *Oct. 3, 2023

(54) ON SITE GENERATED PERFORMIC ACID COMPOSITIONS FOR TEAT TREATMENT

(71) Applicant: ECOLAB USA INC., Saint Paul, MN (US)

(72) Inventors: Junzhong Li, Saint Paul, MN (US); Alexander Thomas, Saint Paul, MN (US); Allison Prideaux, Saint Paul, MN (US); David D. McSherry, Saint Paul, MN (US); Joseph Morelli, Saint Paul, MN (US); Richard Staub, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 46 days.

This patent is subject to a terminal disclaimer.

(21) Appl. No.: 17/448,311

(22) Filed: Sep. 21, 2021

(65) Prior Publication Data
US 2022/0000828 A1    Jan. 6, 2022

Related U.S. Application Data

(63) Continuation of application No. 16/442,096, filed on Jun. 14, 2019, now Pat. No. 11,260,040.

(60) Provisional application No. 62/685,670, filed on Jun. 15, 2018.

(51) Int. Cl.
*A61K 31/22* (2006.01)
*A61K 47/10* (2017.01)

(52) U.S. Cl.
CPC .............. *A61K 31/22* (2013.01); *A61K 47/10* (2013.01)

(58) Field of Classification Search
CPC ......... A61K 31/22; A61K 47/10; A01N 37/16
See application file for complete search history.

(56) References Cited

U.S. PATENT DOCUMENTS

| | | | |
|---|---|---|---|
| 598,218 | A | 2/1898 | Going |
| 2,448,252 | A | 8/1948 | Cornthwaite et al. |
| 2,955,905 | A | 10/1960 | Davies et al. |

(Continued)

FOREIGN PATENT DOCUMENTS

| | | | |
|---|---|---|---|
| CA | 2266523 A1 | 9/1999 | |
| CA | 2475361 A1 | 8/2003 | |

(Continued)

OTHER PUBLICATIONS

The Merck Veterinary Manual, 11th Ed, 2016, pp. 1358-1368 (Year: 2016).*

(Continued)

*Primary Examiner* — San Ming R Hui
(74) *Attorney, Agent, or Firm* — McKee, Voorhees & Sease, PLC

(57) ABSTRACT

The present disclosure relates generally to peroxyformic acid forming compositions and methods for forming peroxyformic acid, preferably in situ, and peroxyformic acid formed by said compositions and methods for the purpose of treating an animal tissue and providing an antimicrobial function thereon. present disclosure in particular relates to a residue-free teat treatment composition for the treatment of an animal tissue, especially bovine teats, which provides antimicrobial efficacy and does not leave a non-food ingredient residue on treated teats.

22 Claims, 2 Drawing Sheets

(56) References Cited

U.S. PATENT DOCUMENTS

| | | |
|---|---|---|
| 2,995,524 A | 8/1961 | Wylie et al. |
| 3,169,986 A | 2/1965 | Webb et al. |
| 3,256,198 A | 6/1966 | Matzner |
| 3,272,750 A | 9/1966 | Chase |
| 3,432,546 A | 3/1969 | Oringer et al. |
| 3,847,830 A | 11/1974 | Williams et al. |
| 3,925,234 A | 12/1975 | Hachmann et al. |
| 4,003,841 A | 1/1977 | Hachmann et al. |
| 4,051,058 A | 9/1977 | Böwing et al. |
| 4,126,573 A | 11/1978 | Johnston |
| 4,170,453 A | 10/1979 | Kitko |
| 4,233,235 A | 11/1980 | Camden et al. |
| 4,370,251 A | 1/1983 | Liao et al. |
| 4,412,934 A | 11/1983 | Chung et al. |
| 4,483,778 A | 11/1984 | Thompson et al. |
| 4,486,327 A | 12/1984 | Murphy et al. |
| 4,550,026 A | 10/1985 | Ando |
| 4,617,090 A | 10/1986 | Chum et al. |
| 4,655,781 A | 4/1987 | Hsieh et al. |
| 4,778,618 A | 10/1988 | Fong et al. |
| 4,964,870 A | 10/1990 | Fong et al. |
| 5,030,240 A | 7/1991 | Wiersema et al. |
| 5,063,249 A | 11/1991 | Andrews |
| 5,139,788 A | 8/1992 | Schmidt |
| 5,143,641 A | 9/1992 | Nunn |
| 5,200,189 A | 4/1993 | Oakes et al. |
| 5,246,620 A | 9/1993 | Gethoffer et al. |
| 5,266,587 A | 11/1993 | Sankey et al. |
| 5,314,687 A | 5/1994 | Oakes et al. |
| 5,374,433 A | 12/1994 | Bowling et al. |
| 5,391,324 A | 2/1995 | Reinhardt et al. |
| 5,422,028 A | 6/1995 | Oakes et al. |
| 5,431,849 A | 7/1995 | Damhus et al. |
| 5,463,112 A | 10/1995 | Sankey et al. |
| 5,466,825 A | 11/1995 | Carr et al. |
| 5,503,765 A | 4/1996 | Schepers et al. |
| 5,505,740 A | 4/1996 | Kong et al. |
| 5,576,282 A | 11/1996 | Miracle et al. |
| 5,589,507 A | 12/1996 | Hall, II et al. |
| 5,616,281 A | 4/1997 | Hardy et al. |
| 5,616,335 A | 4/1997 | Nicolle et al. |
| 5,635,195 A | 6/1997 | Hall, II et al. |
| 5,637,755 A | 6/1997 | Nagumo et al. |
| 5,681,805 A | 10/1997 | Scheuing et al. |
| 5,716,923 A | 2/1998 | MacBeath |
| 5,718,910 A | 2/1998 | Oakes et al. |
| 5,817,614 A | 10/1998 | Miracle et al. |
| 5,827,447 A | 10/1998 | Tamura et al. |
| 5,827,808 A | 10/1998 | Appleby et al. |
| 5,840,343 A | 11/1998 | Hall, II et al. |
| 5,914,303 A | 6/1999 | Sankey et al. |
| 5,928,382 A | 7/1999 | Reinhardt et al. |
| 5,977,403 A | 11/1999 | Byers |
| 5,998,350 A | 12/1999 | Burns et al. |
| 6,022,381 A | 2/2000 | Dias et al. |
| 6,049,002 A | 4/2000 | Matilla et al. |
| 6,068,815 A | 5/2000 | Oberleitner et al. |
| 6,153,613 A | 11/2000 | Ono et al. |
| 6,156,156 A | 12/2000 | Rousu et al. |
| 6,177,393 B1 | 1/2001 | McGregor et al. |
| 6,207,632 B1 | 3/2001 | Brooker et al. |
| 6,210,678 B1 | 4/2001 | Richards |
| 6,211,237 B1 | 4/2001 | Huss et al. |
| 6,221,341 B1 | 4/2001 | Montgomery |
| 6,254,801 B1 | 7/2001 | Reinold et al. |
| 6,262,013 B1 | 7/2001 | Smith et al. |
| 6,274,542 B1 | 8/2001 | Carr et al. |
| 6,284,719 B1 | 9/2001 | Simms |
| 6,284,793 B1 | 9/2001 | Fuchs et al. |
| 6,379,685 B1 | 4/2002 | Richter et al. |
| 6,399,564 B1 | 6/2002 | Speed et al. |
| 6,537,958 B1 | 3/2003 | diCapua et al. |
| 6,548,467 B2 | 4/2003 | Baker et al. |
| 6,548,470 B1 | 4/2003 | deBuzzaccarini et al. |
| 6,569,286 B1 | 5/2003 | Withenshaw et al. |
| 6,585,934 B1 | 7/2003 | Oberleitner et al. |
| 6,599,871 B2 | 7/2003 | Smith |
| 6,602,845 B2 | 8/2003 | Connor et al. |
| 6,627,657 B1 | 9/2003 | Hilgren et al. |
| 6,649,140 B2 | 11/2003 | Paparatto et al. |
| 6,689,732 B1 | 2/2004 | Guedira et al. |
| 6,693,069 B2 | 2/2004 | Körber et al. |
| 6,802,061 B1 | 10/2004 | Parthasarathy et al. |
| 6,841,090 B1 | 1/2005 | Serego Allighieri et al. |
| 7,012,154 B2 | 3/2006 | Mineyard et al. |
| 7,061,597 B2 | 6/2006 | Oberleitner et al. |
| 7,189,385 B2 | 3/2007 | Montgomery |
| 7,217,295 B2 | 5/2007 | Samain et al. |
| 7,494,963 B2 | 2/2009 | Ahmed et al. |
| 7,550,420 B2 | 6/2009 | DiCosimo et al. |
| 7,569,232 B2 | 8/2009 | Man et al. |
| 7,612,030 B2 | 11/2009 | DiCosimo et al. |
| 7,682,403 B2 | 3/2010 | Gohl et al. |
| 7,723,083 B2 | 5/2010 | DiCosimo et al. |
| 7,754,460 B2 | 7/2010 | Amin et al. |
| 7,807,425 B2 | 10/2010 | DiCosimo et al. |
| 7,829,315 B2 | 11/2010 | DiCosimo et al. |
| 7,915,445 B2 | 3/2011 | Maatta et al. |
| 7,919,122 B2 | 4/2011 | Okano et al. |
| 7,951,566 B2 | 5/2011 | DiCosimo et al. |
| 7,964,378 B2 | 6/2011 | DiCosimo et al. |
| 8,110,603 B2 | 2/2012 | Kawabata et al. |
| 8,129,153 B2 | 3/2012 | DiCosimo et al. |
| 8,168,676 B2 | 5/2012 | DiCosimo et al. |
| 8,178,581 B2 | 5/2012 | DiCosimo et al. |
| 8,293,792 B2 | 10/2012 | DiCosimo et al. |
| 8,367,728 B2 | 2/2013 | DiCosimo et al. |
| 8,389,575 B2 | 3/2013 | DiCosimo et al. |
| 8,426,634 B2 | 4/2013 | Neas et al. |
| 8,486,679 B2 | 7/2013 | DiCosimo et al. |
| 8,518,675 B2 | 8/2013 | DiCosimo et al. |
| 8,729,296 B2 | 5/2014 | Fast et al. |
| 8,841,098 B2 | 9/2014 | Payne et al. |
| 8,865,436 B2 | 10/2014 | Payne et al. |
| 8,877,354 B2 | 11/2014 | Horiuchi et al. |
| 8,883,485 B2 | 11/2014 | Barnett et al. |
| 9,012,504 B2 | 4/2015 | Olson et al. |
| 9,034,390 B2 | 5/2015 | Kielbania, Jr. |
| 9,040,023 B2 | 5/2015 | Durham et al. |
| 9,044,403 B2 | 6/2015 | Schultz |
| 9,192,909 B2 | 11/2015 | Kraus et al. |
| 9,282,746 B2 | 3/2016 | Amin et al. |
| 9,288,992 B2 | 3/2016 | Li et al. |
| 9,321,664 B2 | 4/2016 | Li et al. |
| 9,518,013 B2 | 12/2016 | Li et al. |
| 9,585,397 B2 | 3/2017 | Li et al. |
| 9,676,711 B2 | 6/2017 | Junzhong et al. |
| 9,701,931 B2 | 7/2017 | Moore |
| 9,750,755 B2 | 9/2017 | Ahmed et al. |
| 9,752,105 B2 | 9/2017 | Stokes et al. |
| 9,820,489 B2 | 11/2017 | Lohrmann et al. |
| 10,010,075 B2 | 7/2018 | Herdt et al. |
| 10,172,351 B2 | 1/2019 | Kraus et al. |
| 10,433,547 B2 | 10/2019 | Li et al. |
| 10,542,751 B2 | 1/2020 | Li et al. |
| 10,555,523 B2 | 2/2020 | McSherry et al. |
| 2002/0119743 A1 | 8/2002 | Hilgren et al. |
| 2002/0128312 A1 | 9/2002 | Hei et al. |
| 2002/0161258 A1 | 10/2002 | Miracle et al. |
| 2003/0047087 A1 | 3/2003 | Phebus et al. |
| 2003/0100469 A1 | 5/2003 | Connor et al. |
| 2003/0180247 A1 | 9/2003 | Morelli et al. |
| 2004/0035537 A1 | 2/2004 | Delmas et al. |
| 2004/0091448 A1 | 5/2004 | Kross |
| 2004/0097410 A1 | 5/2004 | Zheng et al. |
| 2004/0143133 A1 | 7/2004 | Smith et al. |
| 2005/0008526 A1 | 1/2005 | Bianchetti et al. |
| 2005/0109981 A1 | 5/2005 | Tucker et al. |
| 2005/0118940 A1 | 6/2005 | Hilgren et al. |
| 2005/0151117 A1 | 7/2005 | Man et al. |
| 2006/0177518 A1 | 8/2006 | Stevenson et al. |
| 2007/0082832 A1 | 4/2007 | DiCosimo et al. |
| 2007/0093407 A1 | 4/2007 | Bianchetti et al. |
| 2007/0100204 A1 | 5/2007 | Feld et al. |

(56) References Cited

U.S. PATENT DOCUMENTS

| | | |
|---|---|---|
| 2007/0184999 A1 | 8/2007 | DiCosimo et al. |
| 2007/0249712 A1 | 10/2007 | Dee et al. |
| 2007/0274857 A1 | 11/2007 | Okano et al. |
| 2007/0281060 A1 | 12/2007 | James et al. |
| 2008/0029130 A1 | 2/2008 | Concar et al. |
| 2008/0176299 A1 | 7/2008 | Dicosimo et al. |
| 2008/0176784 A1 | 7/2008 | Clowes et al. |
| 2008/0275132 A1 | 11/2008 | McSherry et al. |
| 2009/0018049 A1 | 1/2009 | Stolte et al. |
| 2009/0061017 A1 | 3/2009 | Pedersen et al. |
| 2009/0221704 A1 | 9/2009 | Aksela et al. |
| 2009/0312279 A1 | 12/2009 | Mookerjee et al. |
| 2010/0048448 A1 | 2/2010 | DiCosimo et al. |
| 2010/0084603 A1 | 4/2010 | Narayan et al. |
| 2010/0119669 A1 | 5/2010 | Ben Yehuda et al. |
| 2010/0159028 A1 | 6/2010 | Shultz |
| 2010/0189707 A1 | 7/2010 | Barnett |
| 2010/0286017 A1 | 11/2010 | Righetto |
| 2011/0020472 A1 | 1/2011 | Coughlin |
| 2011/0081693 A1 | 4/2011 | DiCosimo et al. |
| 2011/0136907 A1 | 6/2011 | Dicosimo et al. |
| 2011/0136908 A1 | 6/2011 | DiCosimo et al. |
| 2011/0152368 A1 | 6/2011 | DiCosimo et al. |
| 2011/0152369 A1 | 6/2011 | DiCosimo et al. |
| 2011/0152370 A1 | 6/2011 | DiCosimo et al. |
| 2011/0168567 A1 | 7/2011 | Smith et al. |
| 2011/0169270 A1 | 7/2011 | Todorof |
| 2011/0171062 A1 | 7/2011 | Wolfe |
| 2011/0173897 A1 | 7/2011 | Schneider |
| 2011/0177145 A1 | 7/2011 | Erkenbrecher, Jr. et al. |
| 2011/0177148 A1 | 7/2011 | DiCosimo et al. |
| 2011/0236335 A1 | 9/2011 | DiCosimo et al. |
| 2011/0236336 A1 | 9/2011 | DiCosimo et al. |
| 2011/0236337 A1 | 9/2011 | DiCosimo et al. |
| 2011/0236338 A1 | 9/2011 | DiCosimo et al. |
| 2011/0236339 A1 | 9/2011 | DiCosimo et al. |
| 2011/0300201 A1 | 12/2011 | Becker et al. |
| 2012/0021486 A1 | 1/2012 | Dinu et al. |
| 2012/0036649 A1 | 2/2012 | Auterinen et al. |
| 2012/0070549 A1 | 3/2012 | Gutzmann et al. |
| 2012/0072441 A1 | 3/2012 | True |
| 2012/0136588 A1 | 5/2012 | Kubach |
| 2012/0156155 A1 | 6/2012 | DiCosimo et al. |
| 2012/0156156 A1 | 6/2012 | DiCosimo et al. |
| 2012/0156157 A1 | 6/2012 | DiCosimo et al. |
| 2012/0156158 A1 | 6/2012 | DiCosimo et al. |
| 2012/0156159 A1 | 6/2012 | DiCosimo et al. |
| 2012/0164236 A1 | 6/2012 | Iwasa et al. |
| 2012/0172441 A1 | 7/2012 | Li et al. |
| 2012/0251675 A1 | 10/2012 | Sowa et al. |
| 2013/0111674 A1 | 5/2013 | Yoon |
| 2013/0158117 A1 | 6/2013 | DiCosimo et al. |
| 2013/0171217 A1 | 7/2013 | Chisholm et al. |
| 2013/0203849 A1 | 8/2013 | Ben Yehuda |
| 2013/0247308 A1 | 9/2013 | Duerrschmidt et al. |
| 2013/0261182 A1 | 10/2013 | Payne et al. |
| 2013/0289113 A1 | 10/2013 | Payne et al. |
| 2013/0289114 A1 | 10/2013 | Payne et al. |
| 2013/0289115 A1 | 10/2013 | Payne et al. |
| 2013/0303844 A1 | 11/2013 | Grudo et al. |
| 2014/0113966 A1 | 4/2014 | DiCosimo et al. |
| 2014/0120179 A1 | 5/2014 | Smith et al. |
| 2014/0121272 A1 | 5/2014 | Smith et al. |
| 2014/0127318 A1 | 5/2014 | Larose |
| 2014/0314829 A1 | 10/2014 | Boyd et al. |
| 2014/0338688 A1 | 11/2014 | Boyd et al. |
| 2015/0118167 A1 | 4/2015 | Boyd et al. |
| 2015/0150263 A1 | 6/2015 | Zhu et al. |
| 2015/0182586 A1 | 7/2015 | Baldridge et al. |
| 2015/0265511 A1 | 9/2015 | Boyd et al. |
| 2016/0176815 A1 | 6/2016 | Li et al. |
| 2016/0205946 A1 | 7/2016 | Stauffer et al. |
| 2017/0020130 A1 | 1/2017 | Buschmann et al. |
| 2017/0064949 A1 | 3/2017 | Kraus et al. |
| 2017/0071200 A1 | 3/2017 | McSherry et al. |
| 2017/0081617 A1 | 3/2017 | Allesen-Holm |
| 2017/0118989 A1 | 5/2017 | Oppong et al. |
| 2017/0156321 A1 | 6/2017 | Li et al. |
| 2017/0354116 A1 | 12/2017 | Gradle et al. |
| 2018/0177189 A1 | 6/2018 | Kleine et al. |
| 2018/0242578 A1 | 8/2018 | Li et al. |

FOREIGN PATENT DOCUMENTS

| | | |
|---|---|---|
| CN | 100581361 C | 1/2010 |
| DE | 3504394 A1 | 9/1985 |
| DE | 102015209819 A1 | 12/2016 |
| EP | 0125781 A1 | 1/1987 |
| EP | 0231632 A2 | 8/1987 |
| EP | 0233731 A2 | 8/1987 |
| EP | 0267047 A2 | 5/1988 |
| EP | 0751933 B1 | 1/1997 |
| EP | 0863098 B1 | 2/1998 |
| EP | 1022946 B1 | 9/1998 |
| EP | 1125497 A2 | 6/2003 |
| EP | 1618786 A1 | 4/2004 |
| EP | 1114137 B1 | 7/2004 |
| EP | 1131016 B1 | 2/2005 |
| EP | 1129171 B1 | 8/2005 |
| EP | 2064385 B1 | 9/2007 |
| EP | 1926808 B1 | 7/2011 |
| EP | 2470666 B1 | 7/2014 |
| EP | 2471941 B1 | 9/2015 |
| EP | 2714877 B1 | 7/2017 |
| EP | 2566943 B1 | 9/2017 |
| EP | 3169844 B1 | 12/2018 |
| JP | 62155203 A | 7/1987 |
| JP | 6305920 A | 11/1994 |
| JP | 2008100161 A | 5/2008 |
| JP | 5186989 B2 | 4/2013 |
| WO | 9115474 A1 | 10/1991 |
| WO | 9403395 A1 | 2/1994 |
| WO | 9420424 A1 | 9/1994 |
| WO | 9424869 A1 | 11/1994 |
| WO | 9504128 A1 | 2/1995 |
| WO | 9524388 A1 | 9/1995 |
| WO | 9532625 A1 | 12/1995 |
| WO | 9533816 A1 | 12/1995 |
| WO | 9606532 A1 | 3/1996 |
| WO | 9614384 A1 | 5/1996 |
| WO | 9616148 A1 | 5/1996 |
| WO | 9623858 A1 | 8/1996 |
| WO | 9719594 A1 | 6/1997 |
| WO | 9803513 A1 | 1/1998 |
| WO | 9804659 A3 | 2/1998 |
| WO | 9856988 A1 | 12/1998 |
| WO | 9931215 A1 | 6/1999 |
| WO | 0018228 A1 | 4/2000 |
| WO | 0018521 A1 | 4/2000 |
| WO | 0045639 A1 | 8/2000 |
| WO | 0170030 A2 | 9/2001 |
| WO | 03092919 A1 | 11/2003 |
| WO | 2007031596 A2 | 3/2007 |
| WO | 2007091996 A1 | 8/2007 |
| WO | 2008088873 A1 | 7/2008 |
| WO | 2009117581 A2 | 9/2009 |
| WO | 2010050634 A1 | 5/2010 |
| WO | 2011073115 A1 | 6/2011 |
| WO | 2011089313 A2 | 7/2011 |
| WO | 2011090980 A1 | 7/2011 |
| WO | 2021037294 A2 | 3/2012 |
| WO | 2012084426 A1 | 6/2012 |
| WO | 2012164561 A1 | 12/2012 |
| WO | 2013052431 A1 | 4/2013 |
| WO | 2013184605 A1 | 12/2013 |
| WO | 2015118357 A2 | 8/2015 |
| WO | 2015181287 A1 | 12/2015 |
| WO | 2016100694 A1 | 6/2016 |
| WO | 2016100700 A1 | 6/2016 |
| WO | 2016135351 A1 | 9/2016 |
| WO | 2016162067 A1 | 10/2016 |
| WO | 2017007416 A1 | 1/2017 |

(56) References Cited

FOREIGN PATENT DOCUMENTS

| WO | 2017044806 A1 | 3/2017 |
|----|---------------|--------|
| WO | 2018175305 A1 | 9/2018 |
| WO | 2018208210 A1 | 11/2018 |

OTHER PUBLICATIONS

Carboni-Oerlemans, Chiara, et al., "Hydrolase-catalysed synthesis of peroxycarboxylic acids: Biocatalytic promiscuity for practical applications", Journal of Biotechnology 126, p. 140-151. Apr. 7, 2006.

Dannacher, Josef J., "Catalytic bleach: Most valuable applications for smart oxidation chemistry", Journal of Molecular Catalysis, vol. 251, pp. 159-176. Mar. 20, 2006.

Effkemann et al., "Peroxide Analysis in Laundry Detergents Using Liquid Chromatography", Analytica Chimica Acta 363, pp. 97-103. Jan. 2, 1998.

Hilal, S.H., "Estimation of Hydrolysis Rate Constants of Carboxylic Acid Ester and Phosphate Ester Compounds in Aqueous Systems from Molecular Structure by SPARC", EPA Research and Development, 55 pages, Sep. 2006.

Humphreys et al., "Rate Measurements on Fast Reactions in the Stirred Flow Reactor; the Alkaline Hydrolysis of Methyl and Ethyl Formate", Contribution from the Dept of Chemistry, Columbia University, 4 pages, Aug. 29, 1955.

International Searching Authority, PCT/IB2011/055832 filed Dec. 20, 2011, "The International Search Report and the Written Opinion of the International Searching Authority or the Declaration", 14 pages, dated Aug. 14, 2012.

International Searching Authority, PCT/IB2011/055830 filed Dec. 20, 2011, "The International Search Report and The Written Opinion of the International Searching Authority, of the Declaration", 8 pages, dated Aug. 24, 2012.

Jakob, "Peroxo Compounds, Inorganic", Ullmann's Encyclopedia of Industrial Chemistry, pp. 293-324, 2007.

Klenk, "Peroxy Compounds, Organic", Ullmann's Encyclopedia of Industrial Chemistry, pp. 325-360, 2012.

Leveneur, Sebastien, "Synthesis of peroxypropionic acid from propionic acid and hydrogen peroxide over heterogeneous catalysts", vol. 147, pp. 323-329. 2009.

Maeda, Hatsuo et al "Assessment of Acyl Groups and Reaction Conditions in the Competition between Perhydrolysis and Hydrolysis of Acyl Resorufins for Developing an Indicator Reaction for Fluorometric Analysis of Hydrogen Peroxide", vol. 50, pp. 169-174. Feb. 28, 2002.

Muurinene, Esa, "Organosolv Pulping—A review and distillation study related to peroxyacid pulping", Department of Process Engineering, University of Oulu, 314 pages, May 16, 2000.

Ogata, Y., et al., "The Formation of Peracids by the Perhydrolysis with Alkaline Hydrogen Peroxide", Tetrahedron, vol. 23, pp. 3327-3332. Dec. 13, 1996.

International Searching Authority, "Written Opinion of the International Searching Authority", issued in connection to International Application No. PCT/US2015/066427, 8 pages, dated Apr. 19, 2016.

Rusch, et al., "Biocatalytic Peroxy Acid Formation for Disinfection", Journal of Molecular Catalysis B: Enzymatic 19-20, pp. 499-505. May 16, 2002.

Rusch, et al., "Lipase-Catalyzed Conversions of Trimethylsilyl Ethers: Deprotection, Acetylation, Epoxidation and One-Pot-Multi-Step Reactions", Journal of Molecular Catalysis B: Enzymatic 7, pp. 283-289. Feb. 26, 1999.

Rusch, et al., "Lipase-Catalyzed Preparation of Peroxy Acids and their use for Epoxidation", Journal of Molecular Catalysis A: Chemical 117, pp. 311-319. Dec. 31, 1997.

Safety Data Sheet, "Glycerol Triformate, Technical Grade" Santa Cruz Biotechnology, Inc., 5 pages, Jul. 24, 2017.

Safety Data Sheet, "Glyceryl triacetate", Santa Cruz Biotechnology, Inc., 6 pages, Nov. 6, 2018.

Shekhar, "Facile N-Formylation of amines using Lewis acids as novel catalysts", Tetrahedron Letters, 50, p. 7099-7101, 2009.

Sunburg and Panten, "2 Individual Fragrance and Flavor Materials", Common Fragrance and Flavor Materials, 5th Ed, p. 7-175, 2006.

Tao, Weiyi et al., "Efficient Production of Peracetic Acid in Aqueous Solution with Cephalosporin-Deacetylating Acetyl Xylan Esterase from Bacillus Subtilis", Process Biochemistry, 50, pp. 2121-2127 available online Oct. 23, 2015.

Tsunokawa, Youko et al., "A Versatile Method for Preparation of O-Alkylperoxycarbonic Acids: Epoxidation with Alkyloxycarbonylimidazoles and Hydrogen Peroxide", Tetrahedron Letters, vol. 23, No. 20, pp. 2113-2116, 1982.

Yin (Tyler) DeLu et al., "New Structural Motif for Carboxylic Acid Perhydrolases", Chemistry, vol. 19(9), pp. 3037-3046, manuscript available Feb. 25, 2014.

Yin, et al., "Switching Catalysis From Hydrolysis to Perhydrolysis in Pseudomonas Fluorescnes Esterase", Biochemistry, 49, pp. 1931-1942. Dec. 31, 2010.

Hinds, Fay Carol, "Somatic cell count testing as a tool in evaluating the efficacy of germicidal teat dips", A Thesis submitted in partial fulfillment of the requirement for the degree of Master of Science in Agriculture in the School of Agricultural Sciences and Technology, Cal State University Fresno Aug. 1992.

Color Additive Status List, FDA, https://www.fda.gov/industry/color-additive-inventories/color-additive-status-list, 2015.

\* cited by examiner

ON SITE GENERATED PERFORMIC ACID COMPOSITIONS FOR TEAT TREATMENT

CROSS-REFERENCE TO RELATED APPLICATIONS

This is a continuation of U.S. Pat. No. 11,260,040, issued Mar. 1, 2022, which claims priority under 35 U.S.C. § 119 to Provisional Application U.S. Ser. No. 62/685,670, filed Jun. 15, 2018, both of which are herein incorporated by reference in their entirety including without limitation, the tables, examples, and claims.

FIELD OF THE INVENTION

The present disclosure relates generally to the treatment of an animal tissue such as a skin surface using peroxyformic acid. An aspect of this invention relates to a coating and/or dip for the teats of dairy cattle to protect the teats from mastitis-causing microorganisms before and between milking. An aspect of this invention also relates to peroxyformic acid forming compositions and methods for forming and using the same, preferably in situ. The present disclosure in particular relates to a teat treatment composition comprising peroxyformic acid which provides antimicrobial efficacy against mastitis-causing microorganisms, provides stable self-indication chemistry, and is low residue.

BACKGROUND OF THE INVENTION

It is well understood that teat dips and treatments are utilized to protect dairy cattle before and after the milking process from exposure to potentially harmful microorganisms. On an industrial scale, the milking of dairy cattle is largely conducted using a milking machine. The milking machine generally includes: teat cups that surround the teats and withdraw milk by the interaction of two chambers, one inside a liner and one between a metal shell and the outside of the liner; a claw where milk collects as it is withdrawn from the teat; vacuum tubes and a vacuum that provide vacuum suction to the teat cups, removing the milk; a milk tube that removes milk from the claw and delivers it to a milk pail or receiving basin; and a motor which provides the suction for the vacuum. Many milking machines also have an automatic take-off (ATO or detacher) device that removes the machine upon completion of milking. Additionally, many milking machine systems further comprise a computer system that regulates and monitors the milking process, including for example information regarding the bovine, the milk, the vacuum pressure, etc.

In order to optimize the milking process and preserve the health of the dairy cattle, it is critical to prevent exposure to microorganisms which might cause mastitis. Mastitis is an infection of the mammary gland and udder tissue resulting in inflammation, irritation, and reduced milk flow, and can potentially lead to permanent damage to the udders. Mastitis treatment and control is one of the largest costs to the dairy industry and is also a significant factor in dairy cattle welfare. It results in increased costs for several reasons, namely the reduction of milk yield in the cattle, the spoilage of any milk produced due to contamination, labor, veterinary and pharmaceutical costs of treated mastitic cattle and reduction of longevity due to premature culling.

Prevention of mastitis generally occurs by dipping the teats in an antimicrobial solution. Application of an antimicrobial solution may be performed before or after milking, or both. Regardless of application time, a critical function of a teat dip is to prevent mastitis by killing or controlling infectious microorganisms. A number of teat dip products or mastitis control agents are available which have varying degrees of effectiveness. These products generally all contain at least an antimicrobial agent as an active ingredient of the treating solution. Commonly used antimicrobial agents include iodophors, PVP-iodine (a particular iodophor), hypochlorites, chlorine dioxide, chlorinated isocyanurates (chlorinated-S-triazene-trione), bromine, hydroxyquinone, ammonium chloride, chlorhexidine, hexachlorophene, diaphene, cetyl pyridinium chloride, and quaternary ammonium compounds. However, the existing antimicrobial agents often have an irritating effect upon bovine teats and/or the composition leaves an undesirable residue. Additional ingredients added to prevent this irritation, like emollients, and other components like dyes can interfere with the antimicrobial function, rendering the composition unable to provide an ideal kill rate sufficient to prevent mastitis. Further, many of these antimicrobial agents are not stable enough to provide adequate kill more than a few hours after preparation. See, e.g., U.S. Pat. No. 8,388,990.

Additionally, many anti-mastitits compositions commonly used leave a residue which includes ingredients not found naturally in food or milk. It is an objective of the current application to provide a teat dip composition that leaves no residue containing non-food-based ingredients (i.e., the components in the composition and remaining in a residue are naturally found in food or milk), or more preferably is residue free.

It is therefore an object of the present application to provide a treatment composition for the treatment of an animal tissue, especially bovine teats, which provides antimicrobial efficacy.

It is a further object of the present application to provide a treatment composition for the treatment of an animal tissue, especially bovine teats, which does not leave a non-food ingredient residue on treated teats.

It is a still further object to provide a treatment composition for the treatment of animal tissue which comprises a dye that is stable in the treatment composition and provides sufficient indication and coloration when applied to the animal tissue.

It is a further object of the present application to provide a treatment composition for the treatment of animal tissue which is gentle and non-abrasive when applied to the animal tissue.

Other objects, advantages and features of the present invention will become apparent from the following specification taken in conjunction with the accompanying drawings.

BRIEF SUMMARY OF THE PREFERRED EMBODIMENT

The disclosure relates generally to compositions for treating animal tissue, in particular, teat dip compositions, as well as methods of making and using the compositions.

In particular the compositions are peroxyformic acid forming compositions, and the method for forming peroxyformic acid, are preferably in situ.

A preferred embodiment is found in a teat dip composition comprising hydrogen peroxide or a hydrogen peroxide forming compound, an ester of an alcohol and formic acid, and water. In a preferred embodiment, the teat dip composition can comprise a dye.

A preferred embodiment is found in a performic acid forming teat dip composition comprising a first premix and a second premix; wherein the first premix comprises an ester of an alcohol and formic acid; wherein the second premix comprises hydrogen peroxide or a hydrogen peroxide forming compound; wherein the first premix and second premix, when combined provide a performic acid composition having a pH between about 2.5 and about 7. In a preferred embodiment, first premix, second premix or both the first and second premix can comprise a dye.

A preferred embodiment of the invention is found in a method comprising applying a teat dip composition to an animal tissue; wherein the teat dip composition comprises hydrogen peroxide or a hydrogen peroxide forming compound, an ester of an alcohol and formic acid, and water. In a preferred embodiment, the teat dip composition can comprise a dye.

A preferred embodiment of the invention is found in a method comprising applying a teat dip composition to an animal tissue; wherein the teat dip composition has a pH between about 2.5 and about 7 and is prepared by combining a first premix and a second premix; wherein the first premix comprises an ester of an alcohol and formic acid; wherein the second premix comprises hydrogen peroxide or a hydrogen peroxide forming compound. In a preferred embodiment, first premix, second premix or both the first and second premix can comprise a dye.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
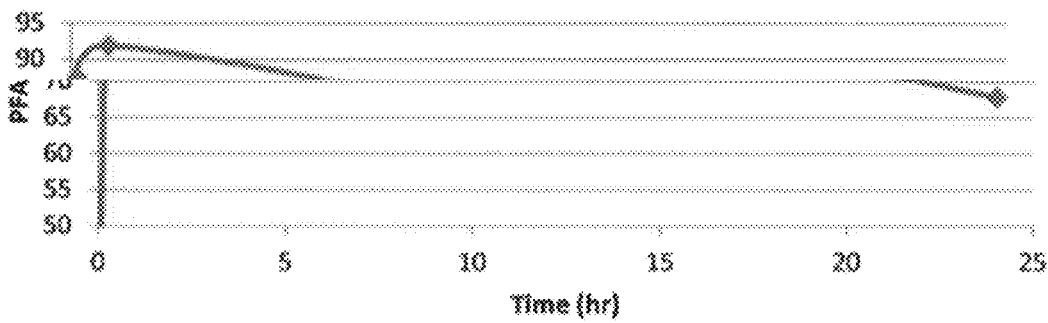
FIG. 1 illustrates generation of peroxyformic acid by a combination of glycerol formates with hydrogen peroxide premixes according to embodiments of the present application.

Various embodiments of the present invention will be described in detail with reference to the figures. Reference to various embodiments does not limit the scope of the invention. Figures represented herein are not limitations to the various embodiments according to the invention and are presented for exemplary illustration of the invention.

DETAILED DESCRIPTION

The embodiments described herein are not limited to particular peroxyformic acid forming compositions, methods for forming peroxyformic acid, the formed peroxyformic acid and methods for using the same as teat dip compositions, which can vary and are understood by skilled artisans. It is further to be understood that all terminology used herein is for the purpose of describing particular embodiments only, and is not intended to be limiting in any manner or scope. For example, all units, prefixes, and symbols may be denoted in its SI accepted form.

Numeric ranges recited within the specification are inclusive of the numbers defining the range and include each integer within the defined range. Throughout this disclosure, various aspects of the compositions and methods are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference. So that the present disclosure may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

It should be noted that, as used in this specification and the appended claims, the singular forms "a," "an," and "the" include plural referents unless the content clearly dictates otherwise. Thus, for example, reference to a composition containing "a compound" includes a composition having two or more compounds. It should also be noted that the term "or" is generally employed in its sense including "and/or" unless the content clearly dictates otherwise.

As used herein, the term "about" refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

The term "cleaning," as used herein, means to perform or aid in soil removal, bleaching, microbial population reduction, or combination thereof. For the purpose of this patent application, successful microbial reduction is achieved when the microbial populations are reduced by at least about 50%, or by significantly more than is achieved by a wash with water. Larger reductions in microbial population provide greater levels of protection.

As used herein, "consisting essentially of" means that the methods and compositions may include additional steps, components, ingredients or the like, but only if the additional steps, components and/or ingredients do not materially alter the basic and novel characteristics of the claimed methods and compositions.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level disinfection" or "high level disinfectant" refers to a compound or composition that kills substantially all organisms, except high levels of bacterial spores, and is affected with a chemical germicide cleared for marketing as a sterilant by the Food and Drug Administration. As used herein, the term "intermediate-level disinfection" or "intermediate level disinfectant" refers to a compound or composition that kills mycobacteria, most viruses, and bacteria with a chemical germicide registered as a tuberculocide by the Environmental Protection Agency (EPA). As used herein, the term "low-level disinfection" or "low level disinfectant" refers to a compound or composition that kills some viruses and bacteria with a chemical germicide registered as a hospital disinfectant by the EPA.

As used herein, the term "free," "no," "substantially no" or "substantially free" refers to a composition, mixture, or ingredient that does not contain a particular compound or to which a particular compound or a particular compound-containing compound has not been added. In some embodiments, the reduction and/or elimination of hydrogen peroxide according to embodiments provide hydrogen peroxide-free or substantially-free compositions. Should the particular compound be present through contamination and/or use in a minimal amount of a composition, mixture, or ingredients, the amount of the compound shall be less than about 3 wt-%. More preferably, the amount of the compound is less than 2 wt-%, less than 1 wt-%, and most preferably the amount of the compound is less than 0.5 wt-%.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

As used herein, "weight percent," "wt-%," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt-%," etc.

It is understood that aspects and embodiments of the invention described herein include "consisting" and/or "consisting essentially of" aspects and embodiments.

As used herein, "animal tissue" refers to the cellular aggregations of a living organism that feeds on organic matter, and can include, but is not limited to, the surface or skin of an animal, particularly a domesticated farm animal, and especially the teats of dairy cattle.

As used herein, "premix" or "pre-mix" describes a mixture of ingredients which is mixed prior to use.

As used herein, "pre-dip" describes a microbiocidal composition applied to the teats before the milking process to contact and kill mastitis-causing pathogens on the teat and/or surrounding area, and applications of the same.

As used herein, "post-dip" describes a microbiocidal composition applied to the teats after the milking process to contact and kill mastitis-causing pathogens on the teat and/or surrounding area, and applications of the same.

As used herein, "milking process" describes the steps involved in milking dairy cattle including, but not limited to, the steps of cleaning the teats (for example, by a pre-dip), drying the teats, foremilk stripping, applying, running, and detaching the milking machine, and treating the teats with a post-milking teat germicide (post-dip).

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present invention will become apparent from the following specification taken in conjunction with the accompanying drawings.

Teat Dip Compositions

This disclosure relates to teat dip compositions and methods of making and using the same. The teat dip compositions comprise peroxyformic acid forming compositions. In one aspect, the present disclosure is directed to peroxyformic acid forming compositions used for treating an animal tissue comprising: a first component comprising hydrogen peroxide or a hydrogen peroxide forming compound; and a second component comprising an ester of an alcohol and formic acid, wherein the first and second components are kept separately prior to use, and when it is time to generate peroxyformic acid, the components are configured to be contacted with each other to form a generated composition comprising peroxyformic acid. In another aspect, the present disclosure is directed to a method for forming peroxyformic acid used for treating an animal tissue comprising: a first component comprising hydrogen peroxide or a hydrogen peroxide forming compound; and a second component comprising an ester of an alcohol and formic acid, wherein the first and second components are kept separately prior to use, and when it is time to generate peroxyformic acid, the components are configured to be contacted with each other to form a generated composition comprising peroxyformic acid.

The present peroxyformic acid forming compositions can comprise any suitable ester of an alcohol and formic acid. Typically, an alcohol refers to a molecule with at least one hydroxyl group (—OH) bound to a carbon atom. An ester of an alcohol and formic acid refers to an ester formed between an alcohol and formic acid. Esters as referred to herein are considered 'water-less' systems as no additional water is added to the esters. In some embodiments, the present peroxyformic acid forming compositions comprise methyl formates, ethyl formates, propyl formates, butyl formates, pentyl formates, heptyl formates, benzyl formates, glycerol formates, pentaerythritol formates, mannitol formates, propylene glycol formates, sorbitol formates and sugar formates. The present peroxyformic acid forming compositions can comprise any suitable sugar formates, e.g., sucrose formates, dextrin formates, maltodextrin formates, or starch formates.

In a preferred embodiment, a liquid reaction employs a glycerol formate, a methyl formate, an ethyl formate, a propyl formate, a butyl formate, a pentyl formate, a heptyl formate, and a benzyl formate. Beneficially, the formates rapidly undergo perhydrolysis for peroxyformic acid generation according to the methods of the invention.

In a preferred embodiment, a reaction employs sugar formates e.g., sucrose formates, dextrin formates, maltodextrin formates, or starch formates. In a still further preferred embodiment, a reaction employs starch formates.

The present peroxyformic acid forming compositions can comprise a ready to use (RTU) system that the direct mixing of the ester premix and H2O2 premix generate performic acid composition for treatment. In some aspects, water was added to the mixture of the ester premix and H2O2 premix during the mixing.

The hydrogen peroxide or hydrogen peroxide forming compound and the ester of an alcohol and formic acid can be configured to be contacted with each other to form a liquid, e.g., a solution, that comprises peroxyformic acid and has any suitable pH, including a pH below about 11, or from about −2 to about 11, or from about 0 to about 11, e.g., about −2 to about −1, −2 to about 0, 0-1, 0-2, 0-3, 0-4, 0-5, 0-6, 0-7, 0-8, 0-9, 0-10, 0-11, 1-2, 1-3, 1-4, 1-5, 1-6, 1-7, 1-8, 1-9, 1-10, 1-11, 2-3, 2-4, 2-5, 2-6, 2-7, 2-8, 2-9, 2-10, 2-11, 3-4, 3-5, 3-6, 3-7, 3-8, 3-9, 3-10, 3-11, 4-5, 4-6, 4-7, 4-8, 4-9, 4-10, 4-11, 5-6, 5-7, 5-8, 5-9, 5-10, 5-11, 6-7, 6-8, 6-9, 6-10, 6-11, 6-7, 7-8, 7-9, 7-10, 7-11, 8-9, 8-10, 8-11, 9-10, 9-11, 10-11, or at about −2, −1, 0, 1, 2, 3, 4, 5, 6, 7, 8, 9, 10 or 11. In some embodiments, the hydrogen peroxide or hydrogen peroxide forming compound and the ester of an alcohol and formic acid are configured to be contacted with each other to form a liquid, e.g., a solution, that comprises peroxyformic acid and has a pH ranging from about −2 to about 11, 0 to about 10, or 5 to about 10, e.g., about −2-0, 0-1, 1-2, 2-3, 3-4, 4-5, 5-6, 5-7, 5-8, 5-9, 5-10, 6-7, 6-8, 6-9, 6-10, 7-8, 7-9, 7-10, 8-9, 8-10, 9-10, or 10-11. In other embodiments, the hydrogen peroxide or hydrogen peroxide forming compound and the ester of an alcohol and formic acid are configured to be contacted with each other to form a liquid, e.g., a solution, that comprises peroxyformic acid and has a pH at about 9. In a preferred aspect, the formed liquid, e.g., a solution, that comprises peroxyformic acid and has a pH near neutral, from about 6-7.

The pH of the formed liquid can become about 8 or lower within about 1 minute after the contact between the hydrogen peroxide or hydrogen peroxide forming compound and the ester of an alcohol and formic acid or after the contact between the solid composition and the liquid. In some embodiments, the pH of the formed liquid can become about 8 or lower within about 1 second, 2 seconds, 3 seconds, 4 seconds, 5 seconds, 6 seconds, 7 seconds, 8 seconds, 9 seconds, 10 seconds, 20 seconds, 30 seconds, 40 seconds, 50 seconds after the contact between the hydrogen peroxide or hydrogen peroxide forming compound and the ester of an alcohol and formic acid or after the contact between the solid composition and the liquid. In other embodiments, the pH of the formed liquid comprising peroxyformic acid becomes about 8 or lower within about 1 minute or less. In an aspect, the pH of the formed liquid comprising peroxyformic acid becomes about 8 or lower within about 45 seconds or less, 40 seconds or less, 35 seconds or less, 30 seconds or less, 25 seconds or less, 20 seconds or less, 15 seconds or less, 10 seconds or less, or 5 seconds or less. In an aspect, the pH of the formed liquid comprising peroxyformic acid becomes about 8 or lower near instantaneously. In other embodiments, the pH of the formed liquid can become about lower than −2, −1, 0, 1, 2, 3, 4, 5, 6, 7, or 8 within about 1 minute after the contact between the hydrogen peroxide or hydrogen peroxide forming compound and the ester of an alcohol and formic acid or after the contact between the solid composition and the liquid.

The liquid that comprises peroxyformic acid can maintain the pH ranging from about −2 to about 8, or from about 0 to about 8 for any suitable time after the contact between the hydrogen peroxide or hydrogen peroxide forming compound and the ester of an alcohol and formic acid, or after the contact between the composition and a liquid. In some embodiments, the liquid that comprises peroxyformic acid maintains the pH ranging from about −2 to about 8, or from about 0 to about 8 from about 1 second to about 10 hours after the contact between the hydrogen peroxide or hydrogen peroxide forming compound and the ester of an alcohol and formic acid or after the contact between the composition and a liquid. For example, the liquid that comprises peroxyformic acid can maintain the pH at about −2, −1, 0, 1, 2, 3, 4, 5, 6, 7, or 8 from about 1 second to about 10 hours after the contact between the hydrogen peroxide or hydrogen peroxide forming compound and the ester of an alcohol and formic acid or after the contact between the composition and a liquid. In another example, the liquid that comprises peroxyformic acid can maintain the pH ranging from about 0 to about 8 for about 1 second, 2 seconds, 3 seconds, 4 seconds, 5 seconds, 6 seconds, 7 seconds, 8 seconds, 9 seconds, 10 seconds, 20 seconds, 30 seconds, 40 seconds, 50 seconds, 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours. In a preferred aspect, the formed liquid, e.g., a solution, that comprises peroxyformic acid and has a pH near neutral, from about 6-7 in a use solution.

In some embodiments, the hydrogen peroxide or hydrogen peroxide forming compound ester of an alcohol and formic acid are configured to be contacted with each other to form a solution that comprises peroxyformic acid and has a pH ranging from about 2 to about 5, e.g., about 2-3, 3-4, or 4-5. hydrogen peroxide or hydrogen peroxide forming compound ester of an alcohol and formic acid hydrogen peroxide or hydrogen peroxide forming compound ester of an alcohol and formic acid. The solution can maintain the pH range for any suitable amount of time, e.g., from about 1 minute to about 24 hours. For example, the solution can maintain the pH range from about 4 to about 8 or 9 for at least about 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours. The solution may be formed at a temperature ranging from about 0° F. to about 120° F., for example about 0° F. to about 100° F., and/or about 32° F. to about 120° F.

The present peroxyformic acid forming compositions can further comprise a catalyst (e.g. mineral acid) or an enzyme that catalyzes formation of peroxyformic acid from the ester of an alcohol and formic acid, and hydrogen peroxide. The present peroxyformic acid forming compositions can comprise any suitable catalyst, e.g., a strong mineral acid, or enzyme, e.g., a perhydrolytic enzyme, lipase, coronase, termanyl or esperease. The catalyst or an enzyme can be comprised in any suitable part of the present peroxyformic acid forming compositions. In some embodiments, the hydrogen peroxide or hydrogen peroxide forming compound comprises the catalyst or enzyme. In other embodiments, the ester of an alcohol and formic acid comprises the catalyst or enzyme. In still other embodiments, the present peroxyformic acid forming compositions can further comprise a third reagent that comprises the catalyst or enzyme. In yet other embodiments, the solid composition comprises the catalyst or enzyme.

In another embodiment the present peroxyformic acid forming compositions are free of a catalyst.

The present peroxyformic acid forming compositions can comprise any suitable pH buffering agent. Suitable buffer agents include but are not limited to organic acids, such as citric acid, lactic acid, acetic acid, succinic acid, salts thereof, and combinations thereof. Preferred buffering agents include, but are not limited to, succinic acid salts such as disodium succinate. Exemplary buffer agents suitable for using with a liquid ester can be an organic amine, such as triethanol amine, imidazole, etc. Exemplary buffer agents suitable for using with a solid form of ester include a broader range of buffers, such as a carbonate salt, a phosphate salt, etc. The pH buffer reagent can be comprised in any suitable part of the present peroxyformic acid forming compositions. In some embodiments, the hydrogen peroxide or hydrogen peroxide forming compound comprises a pH buffering agent. In other embodiments, the present peroxyformic acid forming compositions can further comprise a third reagent that comprises a pH buffering agent. In still other embodiments, the solid composition comprises a pH buffering agent.

The teat dip compositions can comprise any suitable stabilizing agent for hydrogen peroxide and/or performic acid. Exemplary stabilizing agents for hydrogen peroxide/performic acid include phosphonates, heterocyclic carboxylic acids and the mixtures thereof. In some embodiments, stabilizing agents for hydrogen peroxide can be Dequest 2010, Dequest 2066, Dipicolinic acids, picolinic acids etc. The stabilizing agent for hydrogen peroxide/performic acid can be comprised in any suitable part of the present peroxyformic acid forming compositions. In some embodiments, the ester of an alcohol and formic acid comprises a stabilizing agent for hydrogen peroxide. In other embodiments, the present peroxyformic acid forming compositions can further comprise a third reagent that comprises a stabilizing agent for hydrogen peroxide/performic acid. In still other embodiments, the solid composition comprises a stabilizing agent for hydrogen peroxide/performic acid.

The teat dip compositions can comprise any suitable number of dosage(s) of the hydrogen peroxide or hydrogen peroxide forming compound that is kept separately prior to use and is used to contact the ester of an alcohol and formic acid that comprises hydrogen peroxide. For example, the present peroxyformic acid forming compositions can comprise a single dosage of the hydrogen peroxide or hydrogen peroxide forming compound that is kept separately prior to use and is used to contact the ester of an alcohol and formic acid that comprises hydrogen peroxide. In another example, the present peroxyformic acid forming compositions can comprise multiple dosages of the hydrogen peroxide or hydrogen peroxide forming compound that are kept separately prior to use and are used to contact the ester of an alcohol and formic acid that comprises hydrogen peroxide, either simultaneously or sequentially. The multiple dosages of the hydrogen peroxide or hydrogen peroxide forming compound can comprise any suitable ester(s) of an alcohol and formic acid. For example, the multiple dosages of the hydrogen peroxide or hydrogen peroxide forming compound can comprise the same ester of an alcohol and formic acid. In another example, the multiple dosages of the hydrogen peroxide or hydrogen peroxide forming compound can comprise different esters of alcohols and formic acid. The multiple dosages of the hydrogen peroxide or hydrogen peroxide forming compound can comprise the same or different concentrations of ester(s) of an alcohol and formic acid. In still another example, the present peroxyformic acid forming compositions can comprise multiple dosages of the solid composition that are kept separately prior to use.

The present peroxyformic acid forming compositions can comprise any suitable concentration of an ester of an alcohol and formic acid. For example, the hydrogen peroxide or hydrogen peroxide forming compound of the peroxyformic acid forming composition can comprise any suitable concentration of hydrogen peroxide or hydrogen peroxide forming compound. In some embodiments, the formed liquid is a concentrate and comprises the hydrogen peroxide or hydrogen peroxide forming compound in an amount up to about 90%. In other embodiments, the formed liquid comprises the hydrogen peroxide or hydrogen peroxide forming compound in an amount from about 1 ppm to about 2 wt. % of an ester of an alcohol and formic acid, or from about 10 ppm to about 2 wt. % ppm of an ester of an alcohol and formic acid. For example, the hydrogen peroxide or hydrogen peroxide forming compound in the formed liquid can comprise from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500 ppm-1 wt. %, or 1-2 wt. %.

In another example, the solid composition of the peroxyformic acid forming composition can comprise any suitable concentration of hydrogen peroxide or hydrogen peroxide forming compound. In some embodiments, the solid composition can provide a concentrate formed liquid that comprises the hydrogen peroxide or hydrogen peroxide forming compound in an amount up to about 90% of hydrogen peroxide or hydrogen peroxide forming compound. In other embodiments, the solid composition can provide for the formed liquid from about 1 ppm to about 2 wt. % of hydrogen peroxide or hydrogen peroxide forming compound. For example, the solid composition can provide for the formed liquid hydrogen peroxide or hydrogen peroxide forming compound in amounts comprising from about 1 ppm to about 500 ppm of an ester of an alcohol and formic acid, or from about 10 ppm to about 500 ppm of an ester of an alcohol and formic acid. For example, the hydrogen peroxide or hydrogen peroxide forming compound in the formed liquid can comprise from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, or 450-500 ppm, 500 ppm-1 wt. %, or 1-2 wt. %.

The present peroxyformic acid forming compositions can comprise any suitable concentration of an ester of an alcohol and formic acid. For example, the ester of an alcohol and formic acid of the peroxyformic acid forming composition can comprise any suitable concentration of hydrogen peroxide. In some embodiments, a concentrate formed liquid comprises the ester of an alcohol and formic acid in an amount up to about 10%. In some embodiments, the formed liquid comprises the ester of an alcohol and formic acid in an amount comprising 1 ppm to about 500 ppm of an ester of an alcohol and formic acid, or from about 10 ppm to about 500 ppm of an ester of an alcohol and formic acid. For example, the ester of an alcohol and formic acid in the formed liquid can comprise from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, or 450-500 ppm of the ester of an alcohol and formic acid.

In some embodiments, a concentrate formed liquid comprises the ester of an alcohol and formic acid in an amount up to about 10%. In another example, the solid composition can comprise a substance at an amount or concentration that generates from about 1 ppm to about 500 ppm of an ester of an alcohol and formic acid upon contact with a liquid in the formed liquid. For example, the solid composition can comprise a substance at an amount or concentration that generates from about 1 ppm to about 500 ppm of an ester of an alcohol and formic acid, or from about 10 ppm to about 500 ppm of an ester of an alcohol and formic acid. For example, the ester of an alcohol and formic acid in the formed liquid can comprise from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, or 450-500 ppm.

The present peroxyformic acid forming compositions can be configured to form a liquid, e.g., a solution, that comprises any suitable concentration of peroxyformic acid. For example, the hydrogen peroxide or hydrogen peroxide forming compound and the ester of an alcohol and formic acid in the present peroxyformic acid forming compositions can be configured to be contacted with each other to form a liquid and/or solid, e.g., a solution, that comprises any suitable concentration of peroxyformic acid. In some embodiments, the hydrogen peroxide or hydrogen peroxide forming compound and the ester of an alcohol and formic acid can be configured to be contacted with each other to form a liquid, e.g., a solution, that comprises from about 1 ppm to about 500 ppm of peroxyformic acid, from about 1 ppm to about 500 ppm of peroxyformic acid, or from about 10 ppm to about 500 ppm of peroxyformic acid. For example, the peroxyformic acid in the formed liquid can comprise from about 60-500 ppm, preferably 70-450 ppm, more preferably 70-400 ppm, and most preferably 70-300 ppm.

In another example, the solid composition can be configured to be contacted with a liquid to form a solution that comprises from about 1 ppm to about 500 ppm of peroxyformic acid, from 1 ppm to about 500 ppm of peroxyformic acid, or from about 10 ppm to about 500 ppm of peroxyformic acid. For example, the peroxyformic acid in the formed solution can comprise from about 60-500 ppm, 70-450 ppm, 70-400 ppm of peroxyformic acid within 20 minutes of the contact time, more preferably 15 minutes of the contact time, most preferably 10 minutes of the contact time.

In an aspect, at least about 70 ppm or at least about 270 ppm peroxyformic is generated within about 20 minutes or less of contacting the hydrogen peroxide or hydrogen peroxide forming compound and the ester of an alcohol and formic acid.

The present peroxyformic acid forming compositions can be configured to form a liquid, e.g., a solution, that comprises any suitable percentage of peroxyformic acid within any suitable time. For example, the hydrogen peroxide or hydrogen peroxide forming compound and the ester of an alcohol and formic acid in the present peroxyformic acid forming compositions can be configured to be contacted with each other to form a liquid, e.g., a solution, that comprises any suitable concentration of peroxyformic acid within any suitable time. In preferred aspects of the invention the desired concentration of peroxyformic acid is at least 20 ppm, 30 ppm, 40 ppm, 50 ppm, 60 ppm, 65 ppm, 70 ppm, 75 ppm, 80 ppm, 85 ppm, 90 ppm, 95 ppm, 100 ppm, 150 ppm, 200 ppm, 250 ppm, 270 ppm, 300 ppm, 400 ppm, 500 ppm, or more.

The present peroxyformic acid forming compositions can further comprise a $C_2$-$C_{22}$ percarboxylic acid, and wherein the hydrogen peroxide or hydrogen peroxide forming compound or the solid composition comprising the hydrogen peroxide or hydrogen peroxide forming compound and the ester of an alcohol and formic acid are kept separately from the $C_2$-$C_{22}$ percarboxylic acid prior to generate peroxyformic acid. The present peroxyformic acid forming compositions can comprise any suitable $C_2$-$C_{22}$ percarboxylic acid, e.g., peroxyacetic acid, peroxyoctanoic acid and/or peroxysulfonated oleic acid.

In some embodiments, the present peroxyformic acid forming compositions do not comprise a perhyrolysis enzyme. For example, in some cases, the present peroxyformic acid forming compositions do not comprise a member of family 7 of the carbohydrate esterases (CE-7) or a perhyrolysis enzyme that is disclosed in U.S. patent application 2013/0289113.

The teat dip compositions can be concentrated compositions or ready-to-use compositions. Ready-to-use compositions preferably have between about 90.0 wt. % and about 99.9 wt. % water. Concentrated compositions preferably have between about 50 wt. % water and about 99 wt. % water, more preferably between about 65 wt. % and about 99 wt. %, and most preferably between about 80 wt. % and about 99 wt. %. In some embodiments, the concentrated compositions can be applied directly the animal tissue without further dilution. In some embodiments, the concentrated compositions are diluted with water or another diluent to form a use composition. Ready-to-use compositions and use compositions have the same amount of water, i.e., between about 90.0 wt. % and about 99.9 wt. % water.

In a preferred embodiment, the teat dip compositions are low residue and leave no residue containing non-food-based ingredients (i.e., the components in the composition and remaining in a residue are naturally found in food or milk). In a more preferred embodiment, the teat dip compositions are residue-free, i.e., leave no residue.

Methods for Forming Peroxyformic Acid

In another aspect, the present disclosure is directed to method of forming peroxyformic acid compositions used for treating an animal tissue, i.e., the teat dip compositions, comprising: a first component comprising hydrogen peroxide or a hydrogen peroxide forming compound; and a second component comprising an ester of an alcohol and formic acid, wherein the first and second components are kept separately prior to use, and when it is time to generate peroxyformic acid, the components are configured to be contacted with each other to form a generated composition comprising peroxyformic acid.

In some embodiments, the present methods comprise contacting a hydrogen peroxide or hydrogen peroxide forming compound that comprises an ester of an alcohol and formic acid, and a ester of an alcohol and formic acid that comprises hydrogen peroxide or that comprises a substance that generates hydrogen peroxide when in contact with a liquid to form a liquid that comprises peroxyformic acid and has a pH below about 11, or from −2 to about 11, or from 0 to about 11 (or any range therein), wherein said hydrogen peroxide or hydrogen peroxide forming compound and said ester of an alcohol and formic acid are kept separately prior to said contacting and pH of said formed liquid becomes about 8 or lower within about 1 minute after the contact between said hydrogen peroxide or hydrogen peroxide forming compound and said ester of an alcohol and formic acid. In other embodiments, the present methods comprise contacting a solid composition that comprises a hydrogen peroxide or hydrogen peroxide forming compound that comprises an ester of an alcohol and formic acid, and a ester of an alcohol and formic acid that comprises a substance that generates hydrogen peroxide when in contact with a liquid with a liquid to form a liquid that comprises peroxyformic acid and has a pH below about 11, or from −2 to about 11, or from 0 to about 11, and pH of said formed liquid becomes about 8 or lower within about 1 minute after the contact between said solid composition and said liquid.

Any suitable ester of an alcohol and formic acid can be used in the present methods. Typically, an alcohol refers to a molecule with one or more hydroxyl (—OH) groups. An ester of an alcohol and formic acid refers to an ester formed between an alcohol and formic acid. In some embodiments, methyl formates, ethyl formates, propyl formates, butyl formates, pentyl formates, heptyl formates, benzyl formates, glycerol formates, pentaerythritol formates, mannitol formates, propylene glycol formates, sorbitol formates and sugar formates can be used in the present methods. Any suitable sugar formates can be used in the present methods, e.g., sucrose formates, dextrin formates, maltodextrin formates, or starch formates.

The hydrogen peroxide or hydrogen peroxide forming compound or ester of an alcohol and formic acid used in the present methods can have any suitable pH range. For example, the hydrogen peroxide or hydrogen peroxide forming compound or ester of an alcohol and formic acid can have a pH ranging from about 2 to about 6, e.g., about 2-3, 3-4, or 4-5, or 5-6.

The hydrogen peroxide or hydrogen peroxide forming compound and the ester of an alcohol and formic acid can be contacted with each other to form a liquid, e.g., a solution, that comprises peroxyformic acid and has any suitable pH below about 11, or from −2 to about 11, or from about 0 to about 11, e.g., about −2 to about −1, −1-0, 0-1, 0-2, 0-3, 0-4, 0-5, 0-6, 0-7, 0-8, 0-9, 0-10, 0-11, 1-2, 1-3, 1-4, 1-5, 1-6, 1-7, 1-8, 1-9, 1-10, 1-11, 2-3, 2-4, 2-5, 2-6, 2-7, 2-8, 2-9, 2-10, 2-11, 3-4, 3-5, 3-6, 3-7, 3-8, 3-9, 3-10, 3-11, 4- 5, 4-6, 4-7, 4-8, 4-9, 4-10, 4-11, 5-6, 5-7, 5-8, 5-9, 5-10, 5-11, 6-7, 6-8, 6-9, 6-10, 6-11, 6-7, 7-8, 7-9, 7-10, 7-11, 8-9, 8-10, 8-11, 9-10, 9-11, 10-11, or at about −2, −1, 0, 1, 2, 3, 4, 5, 6, 7, 8, 9, 10 or 11.

In some embodiments, the hydrogen peroxide or hydrogen peroxide forming compound and the ester of an alcohol and formic acid are contacted with each other to form a liquid, e.g., a solution, that comprises peroxyformic acid and has a pH ranging from about 2 to about 6, e.g., about 2-3, 3-4, or 4-5, 5-6. In The a solid composition can be contacted with a liquid to form a liquid, e.g., a solution, that comprises peroxyformic acid and has any suitable pH ranging from about 2 to about 5, e.g., about 2-3, 3-4, or 4-5, 5-6.

The liquid that comprises peroxyformic acid can maintain the pH ranging from about 2 to about 5 for any suitable time after the contact between the hydrogen peroxide or hydrogen peroxide forming compound and the ester of an alcohol and formic acid, or after the contact between the composition and a liquid.

In other embodiments, the solid composition can be contacted with a liquid to form a solution that comprises peroxyformic acid and has a pH ranging from about 2 to about 5, e.g., about 2-3, 3-4, or 4-5. In one example, the solid composition is contacted with a liquid to form a solution that comprises peroxyformic acid and has a pH ranging from about 2 to about 5.

The hydrogen peroxide or hydrogen peroxide forming compound and the ester of an alcohol and formic acid can be contacted with each other to form a liquid, e.g., a solution, that comprises peroxyformic acid under any suitable conditions or temperature. In some embodiments, the hydrogen peroxide or hydrogen peroxide forming compound and the ester of an alcohol and formic acid can be contacted with each other to form a liquid, e.g., a solution, that comprises peroxyformic acid under ambient conditions. In other embodiments, the hydrogen peroxide or hydrogen peroxide forming compound and the ester of an alcohol and formic acid can be contacted with each other to form a liquid, e.g., a solution, that comprises peroxyformic acid at a temperature ranging from about 0° F. to about 120° F., for example about 0° F. to about 100° F., and/or about 32° F. to about 120° F.

The present methods can further comprise using a catalyst or an enzyme that catalyzes formation of peroxyformic acid from the ester of an alcohol and formic acid, and hydrogen peroxide. The present methods can use any suitable catalyst or enzyme, e.g., a perhydrolytic enzyme, lipase, coronase, termanyl or esperease. The catalyst or an enzyme can be comprised in any suitable reagent. In some embodiments, the hydrogen peroxide or hydrogen peroxide forming compound comprises the catalyst or enzyme. In other embodiments, the ester of an alcohol and formic acid comprises the catalyst or enzyme. In still other embodiments, the present methods can further comprise using a third reagent that comprises the catalyst or enzyme. In yet other embodiments, the solid composition comprises the catalyst or enzyme.

The present methods can further comprise using a stabilizing agent for peroxyformic acid, a stabilizing agent for hydrogen peroxide, and/or a pH buffering agent. The present methods can use any suitable stabilizing agent. Exemplary stabilizing agents include a phosphonate salt(s) and/or a heterocyclic dicarboxylic acid, e.g., dipicolinic acid. In some embodiments, the stabilizing agent is pyridine carboxylic acid based stabilizers, such as picolinic acid and salts, pyridine-2,6-dicarboxylic acid and salts, and phosphonate based stabilizers, such as phosphoric acid and salts, pyrophosphoric acid and salts and most commonly 1-hydroxyethylidene-1,1-diphosphonic acid (HEDP) and salts. In other embodiments, the present methods can use two or more stabilizing agents, e.g., HEDP and 2,6-pyridinedicarboxylic acid (DPA).

The stabilizing agent(s) can be comprised in any suitable reagent. In some embodiments, the hydrogen peroxide or hydrogen peroxide forming compound comprises a stabilizing agent for peroxyformic acid and/or a pH buffering agent. In other embodiments, the ester of an alcohol and formic acid comprises a stabilizing agent for hydrogen peroxide. In still other embodiments, the present methods can further comprise using a third reagent that comprises a stabilizing agent for peroxyformic acid, a stabilizing agent for hydrogen peroxide, and/or a pH buffering agent. In yet other embodiments, the solid composition comprises a stabilizing agent for peroxyformic acid, a stabilizing agent for hydrogen peroxide, and/or a pH buffering agent.

The present methods can use any suitable pH buffering agent. The pH buffer reagent can include any reagent that is compatible with the ester(s) used in the present methods. Suitable buffer agents include but are not limited to organic acids, such as citric acid, lactic acid, acetic acid, succinic acid, salts thereof, and combinations thereof. Preferred buffering agents include, but are not limited to, succinic acid salts such as disodium succinate. Exemplary buffer agents suitable for using with a liquid ester can be an organic amine, such as triethanol amine, imidazole, etc. Exemplary buffer agents suitable for using with a solid form of ester include a broader range of buffers, such as a carbonate salt, a phosphate salt, etc. The pH buffer reagent can be comprised in any suitable reagent. In some embodiments, the hydrogen peroxide or hydrogen peroxide forming compound comprises a pH buffering agent. In other embodiments, the solid composition comprises a pH buffering agent.

The present methods can use any suitable stabilizing agent for hydrogen peroxide. Exemplary stabilizing agents for hydrogen peroxide include phosphonates, heterocyclic carboxylic acids and the mixtures thereof. In some embodiments, stabilizing agents for hydrogen peroxide can be Dequest 2010, Dequest 2066, Dipicolinic acids, etc. The stabilizing agent for hydrogen peroxide can be comprised in any suitable reagent. In some embodiments, the ester of an alcohol and formic acid comprises a stabilizing agent for hydrogen peroxide. In other embodiments, the present methods can further comprise using a third reagent that comprises a stabilizing agent for hydrogen peroxide. In still other embodiments, the solid composition comprises a stabilizing agent for hydrogen peroxide.

The present methods can use any suitable number of dosage(s) of the hydrogen peroxide or hydrogen peroxide forming compound that is kept separately prior to use and is used to contact the ester of an alcohol and formic acid that comprises hydrogen peroxide. For example, the present methods can use a single dosage of the hydrogen peroxide or hydrogen peroxide forming compound that is kept separately prior to use and is used to contact the ester of an alcohol and formic acid that comprises hydrogen peroxide. In another example, the present methods can use multiple dosages of the hydrogen peroxide or hydrogen peroxide forming compound that are kept separately prior to use and are used to contact the ester of an alcohol and formic acid that comprises hydrogen peroxide, either simultaneously or sequentially. The multiple dosages of the hydrogen peroxide or hydrogen peroxide forming compound comprise any suitable ester(s) of an alcohol and formic acid. For example, the multiple dosages of the hydrogen peroxide or hydrogen peroxide forming compound can comprise the same ester of an alcohol and formic acid. In another example, the multiple dosages of the hydrogen peroxide or hydrogen peroxide forming compound can comprise different esters of alcohols and formic acid. The multiple dosages of the hydrogen peroxide or hydrogen peroxide forming compound can comprise the same or different concentrations of ester(s) of an alcohol and formic acid. In still another example, the present methods can use multiple dosages of the solid composition that are kept separately prior to use.

The present methods can use any suitable concentration of an ester of an alcohol and formic acid. For example, the hydrogen peroxide or hydrogen peroxide forming compound of the peroxyformic acid forming composition can comprise any suitable concentration of an ester of an alcohol and formic acid. In some embodiments, the formed liquid is a concentrate and comprises the hydrogen peroxide or hydrogen peroxide forming compound in an amount up to about 90% of an ester of an alcohol and formic acid to form the peroxyformic acid. In some embodiments, the amount of hydrogen peroxide or hydrogen peroxide forming compound in the formed liquid to generate the peroxyformic acid can comprise from about 1 ppm to about 500 ppm of an ester of an alcohol and formic acid, or from about 10 ppm to about 500 ppm of an ester of an alcohol and formic acid. For example, the hydrogen peroxide or hydrogen peroxide forming compound in the formed liquid can comprise from about 1 ppm to about 500 ppm of an ester of an alcohol and formic acid, or from about 10 ppm to about 500 ppm of an ester of an alcohol and formic acid. For example, the hydrogen peroxide or hydrogen peroxide forming compound in the formed liquid can comprise from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, or 450-500 ppm.

In another example, the solid composition of the peroxyformic acid forming composition can comprise any suitable concentration of an ester of an alcohol and formic acid. In some embodiments, the solid composition can provide for the formed liquid a concentrate comprising up to about 90% of an ester of an alcohol and formic acid to form the peroxyformic acid. In some embodiments, the solid composition can provide for the formed liquid amounts from about 1 ppm to about 500 ppm of an ester of an alcohol and formic acid, or from about 10 ppm to about 500 ppm of an ester of an alcohol and formic acid. For example, the solid composition can provide for the formed liquid amounts from about 1 ppm to about 500 ppm of an ester of an alcohol and formic acid, or from about 10 ppm to about 500 ppm of an ester of an alcohol and formic acid. For example, the hydrogen peroxide or hydrogen peroxide forming compound in the formed liquid can comprise from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, or 450-500 ppm. In other embodiments, the solid composition can comprise sufficient amount of the esters for the formed liquid to comprise from about 1 ppm to about 500 ppm of an ester of an alcohol and formic acid.

The present methods can use any suitable concentration of hydrogen peroxide or a substance that generates hydrogen peroxide upon contact with a liquid. For example, the ester of an alcohol and formic acid of the peroxyformic acid forming composition can comprise any suitable concentration of hydrogen peroxide. In some embodiments, the ester of an alcohol and formic acid can provide for the formed liquid a concentrate comprising up to about 10% of the hydrogen peroxide. In some embodiments, the formed liquid can comprise the ester of an alcohol and formic acid in amounts from about 0.1 ppm to about 100,000 ppm of hydrogen peroxide, or from about 1 ppm to about 100,000 ppm of hydrogen peroxide. For example, the ester of an alcohol and formic acid in the formed liquid can comprise from about 1 ppm to about 500 ppm of an ester of an alcohol and formic acid, or from about 10 ppm to about 500 ppm of an ester of an alcohol and formic acid. For example, the hydrogen peroxide or hydrogen peroxide forming compound in the formed liquid can comprise from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, or 450-500 ppm hydrogen peroxide.

In another example, the solid composition can comprise a substance at an amount or concentration that generates from about 1 ppm to about 500 ppm of hydrogen peroxide, or from about 10 ppm to about 500 ppm of hydrogen peroxide in the formed liquid. For example, the solid composition can comprise a substance at an amount or concentration that generates from about 1 ppm to about 500 ppm of an ester of an alcohol and formic acid, or from about 10 ppm to about 500 ppm of an ester of an alcohol and formic acid. For example, the hydrogen peroxide or hydrogen peroxide forming compound in the formed liquid can comprise from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, or 450-500 ppm hydrogen peroxide in the formed liquid.

The present methods can be used to form a liquid, e.g., a solution, that comprises any suitable concentration of peroxyformic acid. For example, the hydrogen peroxide or hydrogen peroxide forming compound and the ester of an alcohol and formic acid can be contacted with each other to form a liquid, e.g., a solution, that comprises any suitable concentration of peroxyformic acid. In some embodiments, the hydrogen peroxide or hydrogen peroxide forming compound and the ester of an alcohol and formic acid can be contacted with each other to form a liquid, e.g., a solution, that comprises from about 1 ppm to about 500 ppm of peroxyformic acid, from about 1 ppm to about 500 ppm of an ester of an alcohol and formic acid, or from about 10 ppm to about 500 ppm of an ester of an alcohol and formic acid. For example, the hydrogen peroxide or hydrogen peroxide forming compound in the formed liquid can comprise from about 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, or 450-500 ppm.

In another example, the solid composition can be contacted with a liquid to form a solution that comprises from about 0.1 ppm to about 100,000 ppm of peroxyformic acid, from about 0.1 ppm to about 10,000 ppm of peroxyformic acid or from about 0.1 ppm to about 5,000 ppm of peroxyformic acid. In some embodiments, the solid composition can be contacted with a liquid to form a liquid, e.g., a solution, that comprises from about 60 ppm to about 500 ppm of peroxyformic acid, preferably 70-450 ppm, more preferably 70-400 ppm of peroxyformic acid.

The present methods can be used to form a liquid, e.g., a solution, that comprises any suitable concentration of peroxyformic acid within any suitable time. For example, the hydrogen peroxide or hydrogen peroxide forming compound and the ester of an alcohol and formic acid in the present peroxyformic acid forming compositions can be contacted with each other to form a liquid, e.g., a solution, that comprises any suitable concentration of peroxyformic acid within any suitable time. In some embodiments, the hydrogen peroxide or hydrogen peroxide forming compound and the ester of an alcohol and formic acid can be contacted with each other to form a liquid, e.g., a solution, that comprises at least about 1 ppm peroxyformic acid within 20 minutes of the contact time, e.g., at least about 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 150 ppm, 200 ppm, 250 ppm, 270 ppm, 300 ppm, 400 ppm, 500 ppm, 600 ppm, 700 ppm, 800 ppm, 900 ppm, 1,000 ppm, of peroxyformic acid within 20 minutes, 15 minutes, 10 minutes, 5 minutes or 1 minute of the contact time.

In another example, the solid composition can be contacted with a liquid to form a liquid, e.g., a solution, that comprises any suitable concentration of peroxyformic acid within any suitable time. In some embodiments, the solid composition can be contacted with a liquid to form a liquid, e.g., a solution, that comprises at least about 1 ppm peroxyformic acid within 1 minute of the contact time, e.g., at least about 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 150 ppm, 200 ppm, 250 ppm, 270 ppm, 300 ppm, 400 ppm, 500 ppm, of peroxyformic acid within 20 minutes, 15 minutes, 10 minutes, 5 minutes or 1 minute of the contact time.

In an aspect, at least about 60 ppm, 70 ppm, 100 ppm, 150 ppm, 200 ppm, 250 ppm, 270 ppm, 300 ppm, 350 ppm, 400 ppm, 450 ppm, or at least about 500 ppm peroxyformic is generated within about 20 minutes, 15 minutes, 10 minutes, or less of contacting the hydrogen peroxide or hydrogen peroxide forming compound and the ester of an alcohol and formic acid.

In preferred aspects of the invention the desired concentration of peroxyformic acid is 1 ppm, 2 ppm, 3 ppm, 4 ppm, 5 ppm, 6 ppm, 7 ppm, 8 ppm, 9 ppm, 10 ppm, 15 ppm, 20 ppm, 25 ppm, 30 ppm, 35 ppm, 40 ppm, 45 ppm, 50 ppm, 55 ppm, 60 ppm, 65 ppm, 70 ppm, 75 ppm, 80 ppm, 85 ppm, 90 ppm, 95 ppm, 100 ppm, 150 ppm, 200 ppm, 250 ppm, 270 ppm, 300 ppm, 400 ppm, 500 ppm, 600 ppm, 700 ppm, 800 ppm, 900 ppm, 1,000 ppm, ppm or more.

In a preferred embodiment, the hydrogen peroxide or a hydrogen peroxide forming compound is in an amount between about 0.1 wt. % and about 20 wt. %, more preferably between about 0.2 wt. % and about 15 wt. %, most preferably between about 0.2 wt. % and about 12 wt. %.

In a preferred embodiment, the ester of an alcohol and formic acid is in an amount between about 0.5 wt. % and about 10 wt. %, more preferably between about 1 wt. % and about 8 wt. %, most preferably between about 1 wt. % and about 5 wt. %.

In a preferred embodiment, the compositions can be prepared as a concentrated two-part premix. A preferred concentrated first premix comprises an ester of an alcohol and formic acid. A more preferred concentrated first premix comprises an ester of an alcohol and formic acid, and a dye. A preferred concentrated second premix comprises: between about 0.1 wt. % and about 20 wt. % hydrogen peroxide or a hydrogen peroxide forming compound, more preferably between about 0.2 wt. % and about 15 wt. % hydrogen peroxide or a hydrogen peroxide forming compound, most preferably between about 0.2 wt. % and about 12 wt. % hydrogen peroxide or a hydrogen peroxide forming compound; and water. In a most preferred embodiment, a concentrated second premix further comprises one or more of: between about 25 wt. % and about 75 wt. % humectant, more preferably between about 35 wt. % and about 65 wt. % humectant, most preferably between about 45 wt. % and about 55 wt. % humectant; a wetting agent in an amount between about 0.1 wt. % and about 7 wt. %, more preferably between about 0.5 wt. % and about 5 wt. %, most preferably between about 1 wt. % and about 3 wt. %; a stabilizing agent in an amount between about 0.001 wt. % and about 10 wt. %, more preferably between about 0.01 wt. % and about 5 wt. %, most preferably between about 0.1 wt. % an about 1 wt. %; a dye in an amount between about 0.001 wt. % and about 5 wt. %, more preferably between about 0.01 wt. % and about 2 wt. %, most preferably between about 0.1 wt. % and about 1 wt. %; a pH buffering agent between about 0.001 wt. % and about 10 wt. %, more preferably between about 0.01 wt. % and about 5 wt. %, most preferably between about 0.1 wt. % and about 2 wt. %. In a preferred embodiment, the second premix comprises between about 20 wt. % and about 65 wt. % water, more preferably between about 25 wt. % and about 60 wt. % water, most preferably between about 30 wt. % and about 50 wt. % water.

In a preferred embodiment of a concentrated two-part premix, the first premix and second premix are different colors. This can be achieved by one of the premixes containing a dye and the other not containing a dye, or wherein each of the premixes comprise a different dye.

In an embodiment comprising a concentrated two-part premix, the parts can be combined then diluted, or individually diluted then combined. Most preferably, the first and second premix are combined, then diluted.

The present methods can be used to generate peroxyformic acid in any suitable manner or at any suitable location. In some embodiments, the present methods can be used to generate peroxyformic acid in situ for the application of the formed peroxyformic acid.

In some embodiments, the present methods do not comprise using a perhyrolysis enzyme. For example, in some cases, the present methods do not comprise using a member of family 7 of the carbohydrate esterases (CE-7) or a perhyrolysis enzyme that is disclosed in U.S. patent application 2013/0289113.

In another aspect, the present disclosure is directed to peroxyformic acid formed using the present methods, e.g., peroxyformic acid formed in situ for the application of the formed peroxyformic acid.

The peroxyformic acid formed using the present methods (present composition) can further comprise additional percarboxylic acids. Various embodiments of the invention referring to peroxyformic acid compositions and/or peroxyformic acid solutions are further understood to optionally comprise additional percarboxylic acids. As used herein, the term "peracid" may also be referred to as a "percarboxylic acid" or "peroxyacid." The compositions described herein are substantially free, or more preferably free, of sulfoperoxycarboxylic acids, sulfonated peracids and sulfonated peroxycarboxylic acids. A peracid refers to an acid having the hydrogen of the hydroxyl group in carboxylic acid replaced by a hydroxy group. Oxidizing peracids may also be referred to herein as peroxycarboxylic acids.

In some embodiments, peroxyformic acid with other peroxycarboxylic acids can be generated by mixing an ester of an alcohol with a composition comprising peroxycaboxylic acid(s) and hydrogen peroxide to form a composition that comprises both peroxyformic acid and other peroxycarboxylic acids. Examples of compositions comprising both peroxycarboxylic acid and hydrogen peroxide include peroxyacetic acid compositions, peroxyoctanoic acid compositions, etc., all are commercially available from Ecolab Inc. In use, an ester of an alcohol can be contacted, e.g., mixed, with Oxonia Active, Tsunami 100, Matrixx, TurboOxysan and Octave, etc., to form a composition that comprises both peroxyformic acid and other desired peroxycarboxylic acids.

A peracid includes any compound of the formula R—(COOOH)$_n$ in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein.

As used herein, the term "alkyl" includes a straight or branched saturated aliphatic hydrocarbon chain having from 1 to 22 carbon atoms, such as, for example, methyl, ethyl, propyl, isopropyl (1-methylethyl), butyl, tert-butyl (1,1-dimethylethyl), and the like. The term "alkyl" or "alkyl groups" also refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or 'carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

The term "alkenyl" includes an unsaturated aliphatic hydrocarbon chain having from 2 to 12 carbon atoms, such as, for example, ethenyl, 1-propenyl, 2-propenyl, 1-butenyl, 2-methyl-1-propenyl, and the like. The alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like.

Further, as used herein the term "alicyclic" includes any cyclic hydrocarbyl containing from 3 to 8 carbon atoms. Examples of suitable alicyclic groups include cyclopropanyl, cyclobutanyl, cyclopentanyl, etc. The term "heterocyclic" includes any closed ring structures analogous to carbocyclic groups in which one or more of the carbon atoms in the ring is an element other than carbon (heteroatom), for example, a nitrogen, sulfur, or oxygen atom. Heterocyclic groups may be saturated or unsaturated. Examples of suitable heterocyclic groups include for example, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan. Additional examples of suitable heterocyclic groups include groups derived from tetrahydrofurans, furans, thiophenes, pyrrolidines, piperidines, pyridines, pyrrols, picoline, coumaline, etc.

In some embodiments, alkyl, alkenyl, alicyclic groups, and heterocyclic groups can be unsubstituted or substituted by, for example, aryl, heteroaryl, $C_{1-4}$ alkyl, $C_{1-4}$ alkenyl, $C_{1-4}$ alkoxy, amino, carboxy, halo, nitro, cyano, —$SO_3H$, phosphono, or hydroxy. When alkyl, alkenyl, alicyclic group, or heterocyclic group is substituted, preferably the substitution is $C_{1-4}$ alkyl, halo, nitro, amido, hydroxy, carboxy, sulpho, or phosphono. In one embodiment, R includes alkyl substituted with hydroxy. The term "aryl" includes aromatic hydrocarbyl, including fused aromatic rings, such as, for example, phenyl and naphthyl. The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc. The term "heteroaryl" also includes fused rings in which at least one ring is aromatic, such as, for example, indolyl, purinyl, benzofuryl, etc.

In some embodiments, aryl and heteroaryl groups can be unsubstituted or substituted on the ring by, for example, aryl, heteroaryl, alkyl, alkenyl, alkoxy, amino, carboxy, halo, nitro, cyano, —$SO_3H$, phosphono, or hydroxy. When aryl, aralkyl, or heteroaryl is substituted, preferably the substitution is $C_{1-4}$ alkyl, halo, nitro, amido, hydroxy, carboxy, sulpho, or phosphono. In one embodiment, R includes aryl substituted with $C_{1-4}$ alkyl.

Peracids suitable for use include any peroxycarboxylic acids, including varying lengths of peroxycarboxylic and percarboxylic acids (e.g. C1-C22) that can be prepared from the reaction of an ester of an alcohol and formic acid with hydrogen peroxide as described herein. Additional suitable peracids include those of acid-catalyzed equilibrium reaction between a carboxylic acid described above and hydrogen peroxide. A peroxycarboxylic acid can also be prepared by the auto-oxidation of aldehydes or by the reaction of hydrogen peroxide with an acid chloride, acid hydride, carboxylic acid anhydride, or sodium alcoholate. Alternatively, peracids can be prepared through non-equilibrium reactions, which may be generated for use in situ, such as the methods disclosed in U.S. Pat. Nos. 8,846,107 and 8,877,254 each titled "In Situ Generation of Peroxycarboxylic Acids at Alkaline pH, and Methods of Use Thereof," which are incorporated herein by reference. Preferably a composition of the invention includes peroxyformic acid, peroxyacetic acid, peroxyoctanoic acid, peroxypropionic acid, peroxylactic acid, peroxyheptanoic acid, peroxyoctanoic acid and/or peroxynonanoic acid.

In some embodiments, a peroxycarboxylic acid includes at least one water-soluble peroxycarboxylic acid in which R includes alkyl of 1-22 carbon atoms. For example, in one embodiment, a peroxycarboxylic acid includes peroxyformic acid and/or peroxyacetic acid. In another embodiment, a peroxycarboxylic acid has R that is an alkyl of 1-22 carbon atoms substituted with hydroxy. Methods of preparing peroxyacetic acid are known to those of skill in the art including those disclosed in U.S. Pat. No. 2,833,813, which is herein incorporated herein by reference.

In another embodiment, a sulfoperoxycarboxylic acid has the following formula:

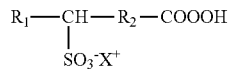

wherein $R_1$ is hydrogen, or a substituted or unsubstituted alkyl group; $R_2$ is a substituted or unsubstituted alkylene group; X is hydrogen, a cationic group, or an ester forming moiety; or salts or esters thereof. In additional embodiments, a sulfoperoxycarboxylic acid is combined with a single or mixed peroxycarboxylic acid composition, such as a sulfoperoxycarboxylic acid with peroxyacetic acid and peroxyoctanoic acid (PSOA/POOA/POAA).

In other embodiments, a mixed peracid is employed, such as a peroxycarboxylic acid including at least one peroxycarboxylic acid of limited water solubility in which R includes alkyl of 5-22 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. Preferably a composition of the invention includes peroxyformic acid, peroxyacetic acid and/or peroxyoctanoic acid. Other combinations of mixed peracids are well suited for use in the current invention.

Advantageously, a combination of peroxycarboxylic acids provides a composition with desirable antimicrobial activity in the presence of high organic soil loads. The mixed peroxycarboxylic acid compositions often provide synergistic micro efficacy. Accordingly, compositions of the invention can include a peroxycarboxylic acid, or mixtures thereof.

Various commercial formulations of peracids are available, including for example, peracetic acid (15%) available from Ecolab Inc. Most commercial peracid solutions state a specific percarboxylic acid concentration without reference to the other chemical components in a use solution. However, it should be understood that commercial products, such as peracetic acid, will also contain the corresponding carboxylic acid (e.g. acetic acid), hydrogen peroxide and water.

Any suitable $C_1$-$C_{22}$ percarboxylic acid can be used in the present compositions. In some embodiments, the $C_1$-$C_{22}$ percarboxylic acid is a $C_2$-$C_{20}$ percarboxylic acid. In other embodiments, the $C_1$-$C_{22}$ percarboxylic is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. In still other embodiments, the $C_1$-$C_{22}$ percarboxylic acid comprises peroxyformic acid, peroxyacetic acid, peroxyoctanoic acid and/or peroxysulfonated oleic acid.

The $C_1$-$C_{22}$ percarboxylic acid can be used at any suitable concentration. In some embodiments, the $C_1$-$C_{22}$ percarboxylic acid has a concentration from about 1 wt-% to about 40 wt-%. In other embodiments, the $C_1$-$C_{22}$ percarboxylic acid has a concentration from about 1 wt-% to about 20 wt-%. In still other embodiments, the $C_1$-$C_{22}$ percarboxylic acid has a concentration at about 1 wt-%, 2 wt-%, 3 wt-%, 4 wt-%, 5 wt-%, 6 wt-%, 7 wt-%, 8 wt-%, 9 wt-%, 10 wt-%, 11 wt-%, 12 wt-%, 13 wt-%, 14 wt-%, 15 wt-%, 16 wt-%, 17 wt-%, 18 wt-%, 19 wt-%, 20 wt-%, 25 wt-%, 30 wt-%, 35 wt-%, or 40 wt-%. In yet other embodiments, the $C_1$-$C_{22}$ percarboxylic acid has a concentration from about 0.1 ppm to about 10,000 ppm, e.g., about 0.1-1 ppm, 1-10 ppm, 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm, 500-550 ppm, 550-600 ppm, 600-650 ppm, 650-700 ppm, 700-750 ppm, 750-800 ppm, 800-850 ppm, 850-900 ppm, 900-950 ppm, 950-1,000 ppm, 1,000-1,500 ppm, 1,500-2,000 ppm, 2,000-2,500 ppm, 2,500-3,000 ppm, 3,000-3,500 ppm, 3,500-4,000 ppm, 4,000-4,500 ppm, or 4,500-5,000 ppm, 5,000-5,500 ppm, 5,500-6,000 ppm, 6,000-6,500 ppm, 6,500-7,000 ppm, 7,000-7,500 ppm, 7,500-8,000, 8,000-8,500 ppm, 8,500-9,000 ppm, 9,000-9,500 ppm, or 9,500-10,000 ppm.

Additional Optional Materials

The present compositions can optionally include additional ingredients to enhance the composition for treating various surfaces and targets according to the invention. Additional optional functional ingredients may include for example, peracid stabilizers, emulsifiers, surfactants, antifoaming agents, foaming agents, humectants, dispersants, solubility modifiers, wetting agents, dyes, rheology modifiers, hydrotropes or couplers, buffers, solvents, acidulants and/or catalysts, additional carboxylic acids, and the like. In some embodiments, no additional functional ingredients are employed.

Viscosity Enhancers

Viscosity enhancers are additional polymers used in water or other water-based fluids used in hydraulic fracturing treatments to provide viscosity enhancement. Natural and/or synthetic viscosity-increasing polymers may be employed in compositions and methods according to the invention. Viscosity enhancers may also be referred to as gelling agents and examples include guar, xanthan, cellulose derivatives, and the like.

In an aspect of the invention, a viscosity enhancer is present in a use solution in an amount between about 1 ppm to about 1,000 ppm, or from about 100 ppm to 1,000 ppm. In a further aspect, a viscosity enhancer is present in a use solution in an amount of at least about 0.01 wt-% to about 10 wt-%, preferably at least about 0.01 wt-% to about 5 wt-%, preferably at least about 0.01 wt-% to about 1 wt-%, at least about 0.01 wt-% to about 2 wt-%, preferably at least about 0.01 wt-% to about 1 wt-%, preferably at least about 0.01 wt-% to about 0.5 wt-%. Beneficially, the compositions and methods of the invention do not negatively interfere with viscosity enhancer included in an aqueous solution.

pH Buffering Agents pH buffering agents may be included as additional functional ingredients in a composition according to the invention. Suitable buffer agents include but are not limited to organic acids, such as citric acid, alctic acid, acetic acid, succinic acid, and combinations thereof. Exemplary buffer agents suitable for using with a liquid ester can be an organic amine, such as triethanol amine, imidazole, etc. Exemplary buffer agents suitable for using with a solid form of ester include a broader range of buffers, such as a carbonate salt, a phosphate salt, etc. The pH buffer reagent can be comprised in any suitable part of the present peroxyformic acid forming compositions. In some embodiments, the hydrogen peroxide or hydrogen peroxide forming compound comprises a pH buffering agent. In other embodiments, the peroxyformic acid forming compositions can further comprise a third reagent that comprises a pH buffering agent. In still other embodiments, the solid composition comprises a pH buffering agent.

In an embodiment the pH buffering agent may comprise a source of alkalinity. The peroxyformic acid forming compositions may require pH adjustment with an alkalinity source. In an exemplary aspect, in the event a reagent of the peracid chemistry includes an acidic component (such as a wetting agent), an alkalinity source may be desirable to increase the strongly acidic pH to ensure the perhydrolysis reaction to generate the peroxyformic acid is not slowed. Suitable sources of alkalinity can include, but is not limited to, an alkaline metal hydroxide, an alkaline earth metal hydroxide, an alkali metal silicate, an alkali metal carbonate, borates, amines, amides or other basic nitrogen sources and mixtures thereof. Suitable alkaline metal hydroxides include, but are not limited to, sodium hydroxide, potassium hydroxide and mixtures thereof. Suitable alkaline earth metal hydroxides include, but are not limited to, magnesium hydroxide, calcium hydroxide and mixtures and derivatives thereof. Suitable alkali metal silicates include but are not limited to, sodium silicate and derivatives thereof. Suitable amines include, but are not limited to, primary, secondary or tertiary amines and diamines carrying at least one nitrogen linked hydrocarbon group, which represents a saturated or unsaturated linear or branched alkyl group having at least 1 carbon atom. Amines may further include alkanolamines including, for example, monoethanolamine, monoisopropanolamine, diethanolamine, diisopropanolamine, triethanolamine, triisopropanolamine and the like.

The pH buffering agents may be employed in amounts sufficient to provide the intended PFA generation kinetic profile, antimicrobial efficacy and/or skin irritation benefits, as may vary depending upon the water source or surface in need of treatment and the contaminants therein. Such agents may be present in a use solution in an amount of at least about 0.001 wt-% to about 10 wt-%.

Wetting Agents

In an aspect, a wetting agent is present in a use solution of the peracid composition in sufficient amounts. Wetting agents function to increase the surface contact or penetration activity of the performic acid composition of the invention. Wetting agents which can be used in the composition of the invention include any of those constituents known within the art to raise the surface activity of the composition of the invention. In an exemplary aspect, the wetting agent is a sulfonic acid or salt thereof (e.g., dioctyl sulfosuccinic acid, sodium salt). In another aspect, the wetting agent is polysorbate-type nonionic surfactants, such as Tween series of surfactants. In certain embodiments, the wetting agent is present in amounts from about 0.001 to about 10 wt-% wetting agent, about 0.01 to about 1 wt-% wetting agent, about 0.01 to about 0.5 wt-% wetting agent, or about 0.1 to about 0.5 wt-% wetting agent.

Dyes

The peroxyformic acid compositions can further comprise a dye which results in the coloring of a target animal tissue, for example a teat. A suitable dye will color the peroxyformic acid compositions and make them more visible upon application, providing an indication of which animal tissue, e.g. teat, has been treated. In an aspect, the compositions of the present application comprise a combination of at least two dyes. In a further aspect, the dye compositions comprise a combination of three dyes. In a further aspect, the combination of dyes provides a visual indication system suitable for detecting the formation or generation of a peroxycarboxylic acid formed in a perhydrolysis reaction. In yet another aspect, the combination of dyes provides a visual indication system using three distinct colors (e.g. blue, green, yellow). In an aspect, the combination of dyes provides a non-fluorescent visual indicator for the peroxycarboxylic acid compositions.

Suitable dyes include oxidizeable dyes, including those insensitive to hydrogen peroxide driving a perhydrolysis reaction to generation a peroxycarboxylic acid composition. In an aspect, the dye composition include a combination of dyes having different half-lives in order to provide sustained visual indicators, such as for up to 7 days, or from 1 to 7 days, or from 12 hours to 7 days. In an aspect, the dye composition include a combination of HRP substrates and synthetic dyes. Suitable chemistries are disclosed in U.S. Ser. No. 62/216,435, which is herein incorporated by reference in its entirety. Preferred dyes include FDC Certified (food grade) dyes. Preferred dyes include dyes which are generally recognized as safe. Suitable dyes include, but are not limited to, FDC Blue #1, FDC Blue #2, FDC Green #3, FDC Red #3, FDC Red #4, FDC Red #40, Violet #1, FDC Yellow #5, and FDC Yellow #6. In a preferred embodiment, FDC Yellow #5 and FDC Yellow #6 is utilized as these dyes surprisingly are stable in the compositions according to the present application.

Humectant

The compositions of the present application can also optionally include one or more humectants. A humectant is a substance having an affinity for water. The humectant can be provided in an amount sufficient to aid in reducing the visibility and presence of a residue either on the animal tissue surface or in a product of the animal tissue (e.g., milk). Accordingly, in some embodiments, the humectant is provided in an amount sufficient to reduce the visibility and presence of a residue as compared to a composition not containing the humectant. The term "residue" refers to the presence of a visible, continuous layer of matter on an animal tissue surface that gives the appearance that the substrate surface is not clean and/or the presence of matter or treatment composition in a product of the animal tissue.

Some example humectants that can be used include those materials that contain greater than 5 wt. % water (based on dry humectant) equilibrated at 50% relative humidity and room temperature. Exemplary humectants that can be used include, but are not limited to alkyl polyglycosides, alpha hydroxy acids, butylene glycol, glycerin, glycerol and other sugar polyols such as sorbitol, xylitol, and malitol, glyceryl triacetate, hexylene glycol, polybetaine polysiloxanes, polyethylene glycol (PEG), polymeric polyols, propylene glycol, silicone, sorbitol, and urea, and mixtures thereof. In some embodiments, the rinse agent composition can include humectant in an amount in the range of up to about 0.0 to 75 wt.-%.

Stabilizing Agents

The present peroxyformic acid forming compositions can further comprise a stabilizing agent for peroxyformic acid, and/or a stabilizing agent for hydrogen peroxide. In an aspect the stabilizing agent(s) are useful in decreasing a pH of the compositions to neutral or lower pH. The present peroxyformic acid forming compositions can comprise any suitable stabilizing agent. In a further aspect the stabilizing agent(s) can also function as a pH buffering agent as described previously. Exemplary stabilizing agents include a phosphonate salt(s) and/or a heterocyclic dicarboxylic acid, e.g., dipicolinic acid. In some embodiments, the stabilizing agent is pyridine carboxylic acid based stabilizers, such as picolinic acid and salts, pyridine-2,6-dicarboxylic acid and salts, and phosphonate based stabilizers, such as phosphoric acid and salts, pyrophosphoric acid and salts and most commonly 1-hydroxyethylidene-1,1-diphosphonic acid (HEDP) and salts. In other embodiments, the present peroxycarboxylic acid forming compositions comprise two or more stabilizing agents, e.g., HEDP and 2,6-pyridinedicarboxylic acid (DPA). In an aspect the stabilizing agent(s) can be comprised in any suitable part of the present peroxyformic acid forming compositions. In some embodiments, the hydrogen peroxide or hydrogen peroxide forming compound comprises a stabilizing agent for the peroxyformic acid and/or a pH buffering agent. In other embodiments, the ester of an alcohol and formic acid comprises a stabilizing agent for hydrogen peroxide. In still other embodiments, the present peroxyformic acid forming compositions can further comprise a third reagent that comprises a stabilizing agent for the peroxyformic acid and/or a stabilizing agent for hydrogen peroxide.

In an aspect, the peroxyformic acid forming compositions can further comprise any suitable stabilizing agent for hydrogen peroxide. Exemplary stabilizing agents for hydrogen peroxide include phosphonates, heterocyclic carboxylic acids and the mixtures thereof. In some embodiments, stabilizing agents for hydrogen peroxide can be Dequest 2010, Dequest 2066, Dipicolinic acids, etc. The stabilizing agent for hydrogen peroxide can be comprised in any suitable part of the peroxyformic acid forming compositions. In some embodiments, the ester of an alcohol and formic acid comprises a stabilizing agent for hydrogen peroxide. In other embodiments, the peroxyformic acid forming compositions can further comprise a third reagent that comprises a stabilizing agent for hydrogen peroxide. In still other embodiments, the solid composition comprises a stabilizing agent for hydrogen peroxide.

In some embodiments, the compositions of the present disclosure include dipicolinic acid as a stabilizing agent. Compositions including dipicolinic acid can be formulated to be free or substantially free of phosphorous. In an aspect of the invention, the stabilizing agent is a pyridine carboxylic acid compound. Pyridine carboxylic acids include dipicolinic acids, including for example, 2,6-pyridinedicarboxylic acid (DPA). In a further aspect, the stabilizing agent is a picolinic acid, or a salt thereof. In an aspect of the invention, the stabilizing agent is a picolinic acid or a compound having the following Formula (IA):

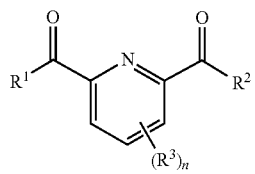

(IA)

wherein $R^1$ is OH or $-NR^{1a}R^{1b}$, wherein $R^{1a}$ and $R^{1b}$ are independently hydrogen or $(C_1-C_6)$alkyl; $R^2$ is OH or $-NR^{2a}R^{2b}$, wherein $R^{2a}$ and $R^{2b}$ are independently hydrogen or $(C_1-C_6)$alkyl; each $R^3$ is independently $(C_1-C_6)$alkyl, $(C_2-C_6)$alkenyl or $(C_2-C_6)$alkynyl; and n is a number from zero to 3; or a salt thereof.

In a further aspect of the invention, the peracid stabilizing agent is a compound having the following Formula (TB):

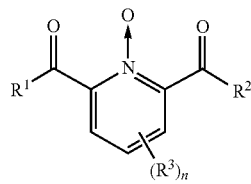

(IB)

wherein $R^1$ is OH or $-NR^{1a}R^{1b}$, wherein $R^{1a}$ and $R^{1b}$ are independently hydrogen or $(C_1-C_6)$alkyl; $R^2$ is OH or $-NR^{2a}R^{2b}$, wherein $R^{2a}$ and $R^{2b}$ are independently hydrogen or $(C_1-C_6)$alkyl; each $R^3$ is independently $(C_1-C_6)$alkyl, $(C_2-C_6)$alkenyl or $(C_2-C_6)$alkynyl; and n is a number from zero to 3; or a salt thereof. Dipicolinic acid has been used as a stabilizer for peracid compositions, such as disclosed in WO 91/07375 and U.S. Pat. No. 2,609,391.

In a further aspect, the stabilizing agent is a phosphate stabilizer or a phosphonate based stabilizer, such as Dequest 2010, Dequest 2066, Dequest 2041, etc. Phosphate based stabilizers are known to act as metal chelators or sequestrants. Conventional phosphate based stabilizing agents include for example, 1-hydroxy ethylidene-1,1-diphosphonic acid $(CH_3C(PO_3H_2)_2OH)$ (HEDP). In other embodiments, the sequestrant can be or include phosphonic acid or phosphonate salt. Suitable phosphonic acids and phosphonate salts include HEDP; ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; picolinic, dipicolinic acid or mixtures thereof. In some embodiments, organic phosphonates, e.g., HEDP are included in the compositions of the present disclosure.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino(tri(methylenephosphonic acid)), $(N[CH_2PO_3H_2]_3)$, available from Monsanto as DEQUEST® 2000; ethylenediamine[tetra(methylenephosphonic acid)] available from Monsanto as DEQUEST® 2041; 2-phosphonobutane-1,2,4-tricarboxylic acid available from Mobay Chemical Corporation, Inorganic Chemicals Division, Pittsburgh, Pa., as Bayhibit® AM; Diethylenetriamine penta(methylene phosphonic acid) available from Stobec, Inc. as DEQUEST® 2066A.

According to various embodiments of the invention, the stabilizing agent can be or include aminocarboxylic acid type sequestrants. Suitable aminocarboxylic acid type sequestrants include the acids or alkali metal salts thereof, e.g., amino acetates and salts thereof. Suitable aminocarboxylates include N-hydroxyethylaminodiacetic acid; hydroxyethylenediaminetetraacetic acid, nitrilotriacetic acid (NTA); ethylenediaminetetraacetic acid (EDTA); N-hydroxyethyl-ethylenediaminetriacetic acid (HEDTA); diethylenetriaminepentaacetic acid (DTPA); and alanine-N,N-diacetic acid; and the like; and mixtures thereof.

According to still further embodiments of the invention, the stabilizing agent can be or include a polycarboxylate. Suitable polycarboxylates include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like.

In other embodiments the stabilizing agent may be a low-phosphate or a phosphate-free stabilizer to provide either low-phosphate or phosphate-free sanitizing and rinsing compositions.

In a still further aspect, a combination of more than one stabilizing agent may be employed. Stabilizing agent(s) may be present in amounts sufficient to provide the intended stabilizing benefits, namely achieving the desired shelf life and/or elevating the SADT of a concentrated peroxycarboxylic acid composition. Stabilizing agents may be present in a concentrated equilibrium peracid composition in amounts from about 0.001 wt-% to about 25 wt-%.

Surfactants

In some aspects of the invention, the peroxyformic acid compositions or one of the reagents employed in forming the peroxyformic acid include at least one surfactant. Surfactants are preferably included to increase solubility of the peroxyformic acid or to maintain the pH of the composition. According to an embodiment of the invention, the surfactant is a hydrotrope coupler or solubilizer, which can be used to ensure that the composition remains phase stable and in a single highly active aqueous form. Such hydrotrope solubilizers or couplers can be used at concentrations that maintain phase stability but do not result in unwanted compositional interaction. Surfactants particularly suitable for use with the compositions of the present disclosure include, but are not limited to, nonionic surfactants, anionic surfactants, amphoteric surfactants and zwitterionic surfactants. Preferably, nonionic and/or anionic surfactants are employed with the peracid compositions of the invention. Exemplary surfactants that can be used are commercially available from a number of sources. For a discussion of surfactants, see Kirk-Othmer, Encyclopedia of Chemical Technology, Third Edition, volume 8, pages 900-912.

Peracids are known to be strong oxidation agents, and as a result many chemicals, including commonly used surfactants are not compatible with concentrated peracids for extended presence of peracids. While it is ideal to use surfactants along with peracids to deliver preferred performance, such as cleaning, wetting et al., there is very limited choice of surfactants that could be put in preformed peracid formulations that meet the minimum shelf life requirements for commercial use. For examples, nonionic surfactants will be degraded by peracids, and cationic surfactants with halogen counter anions will decompose peracids. Some anionic surfactants, namely non-substituted alkyl sulfonates, such as linear alkylbenzensulfonate, liner alkylsulfonate are more compatible with peracids and may be used in some peracids compositions, but these anionic surfactants may not deliver the desired performance owing to their unwanted properties, such as high foam, water hardness tolerance as well as regulation requirements. In contrast, for onsite generated peracid compositions such as disclosed in the present art, all surfactants described above could be coexist with the peracids, as the generated peracids are only stored for very limited time, and typically in hours at the most, and the reactions between the surfactants and the peracids are not significant.

According to a preferred embodiment of the invention, the surfactant is an acidic anionic surfactant. According to a further embodiment, the surfactant is an antimicrobial agent. Exemplary surfactant, hydrotrope solubilizers include anionic surfactants such as an alkyl sulfate, an aryl sulfonate, an alkyl or alkane sulfonate, a linear alkyl benzene or naphthalene sulfonate, a secondary alkane sulfonate, alkyl ether sulfate or sulfonate, an alkyl phosphate or phosphonate, dialkyl sulfosuccinic acid ester, sugar esters (e.g., sorbitan esters) and a $C_{8-10}$ alkyl glucoside.

In some embodiments, the compositions of the present disclosure includes from about 1 wt-% to about 80 wt-% of a surfactant. In other embodiments the compositions of the present disclosure include from about 1 wt-% to about 50 wt-% of a surfactant. In additional embodiments, the compositions of the present disclosure include from about 1 wt-% to about 10 wt-% of a surfactant. In further embodiments, the compositions of the present disclosure or a use solution of the peroxyformic acid composition include about 10 ppm to about 10,000 ppm of a surfactant. In further embodiments, the compositions of the present disclosure or a use solution of the peroxyformic acid composition include about 10 ppm to about 100 ppm of a surfactant. It is to be understood that all ranges and values between these ranges and values are encompassed by the present disclosure.

Nonionic Surfactants

Suitable nonionic surfactants suitable for use with the compositions of the present disclosure include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates; and capped alcohol alkoxylates, such as Plurafac LF221; mixtures thereof, or the like.

Semi-Polar Nonionic Surfactants

The semi-polar type of nonionic surface active agents are another class of nonionic surfactant useful in compositions of the present disclosure. Semi-polar nonionic surfactants include the amine oxides, phosphine oxides, sulfoxides and their alkoxylated derivatives.

Amine oxides are tertiary amine oxides corresponding to the general formula:

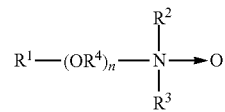

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof; $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20. An amine oxide can be generated from the corresponding amine and an oxidizing agent, such as hydrogen peroxide.

Useful water soluble amine oxide surfactants are selected from the octyl, decyl, dodecyl, isododecyl, coconut, or tallow alkyl di-(lower alkyl)amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl) amine oxide, 3,6,9-trioctadecyldimethylamine oxide and 3-dodecoxy-2-hydroxypropyldi-(2-hydroxyethyl)amine oxide.

Anionic Surfactants

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl)glucamine sulfates, and sulfates of alkylpolysaccharides such as the sulfates of alkylpolyglucoside, and the like. Also included are the alkyl sulfates, alkyl poly(ethyleneoxy)ether sulfates and aromatic poly(ethyleneoxy)sulfates such as the sulfates or condensation products of ethylene oxide and nonyl phenol (usually having 1 to 6 oxyethylene groups per molecule).

Anionic sulfonate surfactants suitable for use in the present compositions also include alkyl sulfonates, the linear and branched primary and secondary alkyl sulfonates, and the aromatic sulfonates with or without substituents.

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of the following formula: R—O—(CH$_2$CH$_2$O)$_n$(CH$_2$)$_m$—CO$_2$X in which R is a C$_8$ to C$_{22}$ alkyl group or

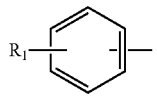

in which R$_1$ is a C$_4$-C$_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In some embodiments, n is an integer of 4 to 10 and m is 1. In some embodiments, R is a C$_8$-C$_{16}$ alkyl group. In some embodiments, R is a C$_{12}$-C$_{14}$ alkyl group, n is 4, and m is 1.

In other embodiments, R is

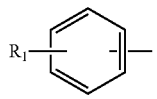

and R$_1$ is a C$_6$-C$_{12}$ alkyl group. In still yet other embodiments, R$_1$ is a C$_9$ alkyl group, n is 10 and m is 1.

Such alkyl and alkylaryl ethoxy carboxylates are commercially available. These ethoxy carboxylates are typically available as the acid forms, which can be readily converted to the anionic or salt form.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphate, or phosphono. Amphoteric surfactants are subdivided into two major classes known to those of skill in the art and described in "Surfactant Encyclopedia" Cosmetics & Toiletries, Vol. 104 (2) 69-71 (1989), which is herein incorporated by reference in its entirety. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Exemplary suitable amphoteric surfactants include long chain imidazole derivatives, including carboxymethylated compounds (glycinates) which are frequently are called betaines. Betaines are a special class of amphoteric discussed herein below in the section entitled, Zwitterion Surfactants. These and other amphoteric surfactants are further described in U.S. patent application Ser. No. 12/568,493, entitled "Sulfoperoxycarboxylic Acids, Their Preparation and Methods of Use as Bleaching and Antimicrobial Agents," hereby expressly incorporated herein in its entirety by reference.

Long chain imidazole derivatives having application in the present disclosure generally have the general formula:

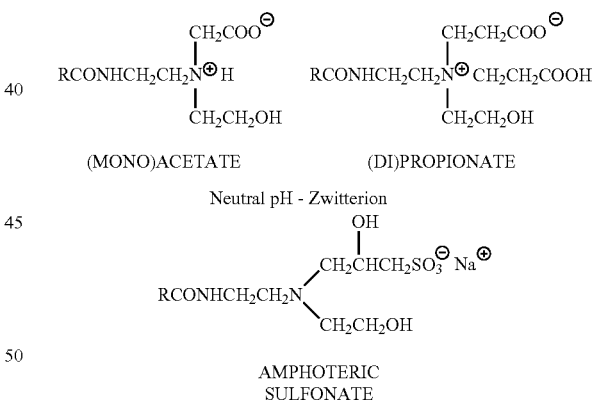

wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines.

Betaines are a special class of amphoteric discussed herein below in the section entitled, Zwitterion Surfactants.

Additionally, suitable amphoteric surfactants include long chain N-alkylamino acids which are readily prepared by reaction $RNH_2$, in which $R=C_8-C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl)alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—CH$_2$—CH$_2$—N$^+$(CH$_2$—CH$_2$—CO$_2$Na)$_2$—CH$_2$—CH$_2$—OH or $C_{12}$-alkyl-C(O)—N(H)—CH$_2$—CH$_2$—N$^+$(CH$_2$—CO$_2$Na)$_2$—CH$_2$—CH$_{2-0}$H. Disodium cocoampho dipropionate is one suitable amphoteric surfactant and is commercially available under the tradename Miranol™ FBS from Rhodia Inc. (Cranbury, N.J). Another suitable coconut derived amphoteric surfactant with the chemical name disodium cocoampho diacetate is sold under the tradename Mirataine™ JCHA, also from Rhodia Inc.

A typical listing of amphoteric classes, and species of these surfactants, is given in U.S. Pat. No. 3,929,678 issued to Laughlin and Heuring on Dec. 30, 1975 and further examples are given in "Surface Active Agents and Detergents" (Vol. I and II by Schwartz, Perry and Berch), each of which are hereby expressly incorporated herein in its entirety by reference.

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A general formula for these compounds is:

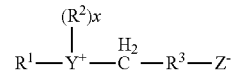

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N-(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S [N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

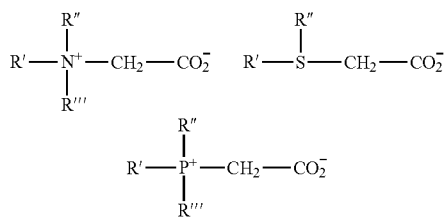

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present disclosure include those compounds having the formula $(R(R^1)_2N^+R^2SO_3^-$, in which R is a $C_6-C_{18}$ hydrocarbyl group, each $R^1$ is typically a $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch). Each of these references are herein incorporated in their entirety.

Alkyl Esters

The compositions may also comprise an alkyl ester. One kind of exemplary alkyl ester includes simple esters, such as, ethyl lactate, or ethyl 2-hydroxypropanoate, or lactic acid ethyl ester. Another kind of exemplary alkyl esters are polysorbates.

Polysorbate is an ester formed by the ethoxylation of sorbitan first, then the addition of lauric acid. It has a following general formula.

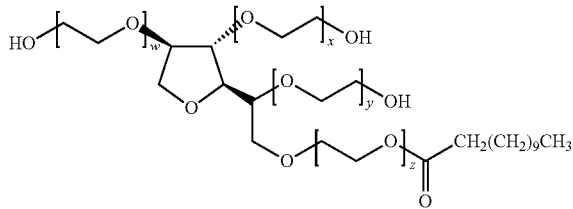

Exemplary polysorbates are polysorbate-20, 60, 80, and 85, whose commercial names are Tween®-20, Tween®-60, Tween®-80, and Tween®-85. The numbers after the name is the total repeat units (the sum of x+y+z+w in the above formula) of polyethylene glycol in the molecule and are distributed across 4 different chains.

In a preferred embodiment, the alkyl ester of the cleaning composition is ethyl lactate, or the decomposition products thereof—lactic acid and ethanol.

In another preferred embodiment, the alkyl ester of the cleaning composition is one or more polysorbates selected from the group of polysorbate-80, polysorbate-20, polysorbate-60, polysorbate-85, or a combination thereof. In some other embodiments, the alkyl ester of the cleaning composition is a polysorbate. In yet some other embodiments, the alkyl ester of the cleaning composition is polysorbate-80.

In some embodiments, the alkyl ester is present in a use solution of the cleaning composition or the cleaning composition itself in an amount of at least about 10 wt-% to about 50 wt-%.

Methods for Treating a Target

In still another aspect, the present disclosure is directed to a method for treating a surface or a target, which method comprises contacting a surface or a target with an effective amount of peroxyformic acid formed using the above methods to form a treated surface or target composition, wherein said treated surface or target composition comprises from about 0.1 ppm to about 1,000 ppm of said peroxyformic acid, and said contacting step lasts for sufficient time to stabilize or reduce microbial population in and/or on said surface or target or said treated surface of target composition.

The peroxyformic acid and the surface or target can be contacted to form a treated target composition comprising any suitable concentration of said peroxyformic acid, e.g., from about 1 ppm to about 500 ppm peroxyformic acid, or from about 60 ppm to about 500 ppm of peroxyformic acid.

For example, the peroxyformic acid in the formed liquid can comprise from about −60-500 ppm, 70-450 ppm, 70-400 ppm of peroxyformic acid.

The present methods can be used for treating any suitable animal tissue including but not limited the skin of a domesticated farm animal, especially the teats of dairy cattle. Any suitable concentration of peroxyformic acid can be used in the present methods. For example, the peroxyformic acid can be used at a concentration from about 50 ppm to about 500 ppm, e.g., at least about 50 ppm, 60 ppm, 65 ppm, 70 ppm, 80 ppm, 85 ppm, 90 ppm, 100 ppm, 150 ppm, 200 ppm, 250 ppm, 270 ppm, 300 ppm, 350 ppm, 400 ppm, 450 ppm, or 500 ppm of peroxyformic acid. In some embodiments, the target is an animal tissue and the contacting step minimizes or does not induce an organoleptic effect in and/or on the animal tissue.

The present methods can be used for treating an animal tissue may include tissue that can be contaminated by a biological fluid, e.g., a biological fluid comprising blood, other hazardous body fluid, or a mixture thereof. In other embodiments, the tissue can be an otherwise contaminated surface.

The peroxyformic acid can be applied in any suitable manner. In some embodiments, the peroxyformic acid can be applied to a target by means of a spray, a fog, or a foam, or by dipping all or part of the target in a composition comprising the peroxyformic acid. In some embodiments, the peroxyformic acid composition is applied to the target by means of a spray, a fog, or a foam. In other embodiments, the diluted peroxyformic acid is applied to the target by applying in the form of a thickened or gelled solution. In still other embodiments, all or part of the target is dipped in the peroxyformic acid composition. The target and/or the peroxyformic acid composition can be subject to any suitable movement to help or facilitate the contact between the target and the peroxyformic acid composition. In some embodiments, the peroxyformic acid composition can be agitated. In other embodiments, the peroxyformic acid composition can be sprayed onto a target, e.g., a bovine teat, under suitable pressure and at a suitable temperature. For example, the peroxyformic acid composition can be sprayed onto a target surface at a pressure of at least 50 psi at a temperature of up to about 60° C., resulting in a contact time of at least 30 seconds.

The present methods can comprise any suitable, additional steps. In some embodiments, the present methods can comprise a vacuum treatment step.

The contacting step in the present methods can last for any suitable amount of time. In some embodiments, the contacting step can last for at least about 10 seconds. For example, the contacting step can last for at least about 10, 20, 30, 40, 50 seconds, 1 minute, 1-2 minutes, 2-3 minutes, 3-4 minutes, 4-5 minutes, 5-6 minutes, 6-7 minutes, 7-8 minutes, 8-9 minutes, or 9-10 minutes, 10-15 minutes, 15-20 minutes, 20-25 minutes, 25-30 minutes, 30-40 minutes, 40-50 minutes, 50-65 minutes, 1-2 hours, 2-3 hours, 3-4 hours, 4-5 hours, 5-6 hours, 6-7 hours, 7-8 hours, 8-9 hours, or 9-10 hours, 16 hours, 1 day, 3 days, 1 week, or longer. In an aspect, the contacting occurs for a period of time before degradation of the peroxyformic acid composition.

In some embodiments, the teat dip composition is a pre-dip composition, which is left on the animal tissue for a brief time, e.g., less than 1 hour, less than 30 minutes, less than 20 minutes, less than 15 minutes, less than 10 minutes, less than 9 minutes, less than 8 minutes, less than 7 minutes, less than 6 minutes, less than 5 minutes, less than 4 minutes, less than 3 minutes, less than 2 minutes, or less than 1 minute. In some embodiments, the teat dip composition is a post-dip composition, which is left on the animal tissue for an extended period of time or without removing. Thus, the methods of using the teat dip compositions can comprise applying a pre-dip composition to an animal and rinsing, washing, or otherwise removing the composition from the animal after a brief time (as set forth above). The methods of using the teat dip compositions can comprise applying a post-dip composition to an animal where the composition is left on the animal or removed after a longer period of time. The methods can comprise both applying a pre-dip composition, removal of the pre-dip composition, and applying a post-dip composition, and optional removal of the post-dip composition.

The present methods can be used to reduce microbial population in and/or on the target or the treated target composition by any suitable magnitude. In some embodiments, the present methods can be used to reduce microbial population in and/or on the target or the treated target composition by at least one $\log_{10}$, two $\log_{10}$, three $\log_{10}$, four $\log_{10}$, five $\log_{10}$, or more. In other embodiments, the level of a microorganism, if present in and/or on the target or the treated target composition, can be stabilized or reduced by the present methods. For example, at least 10%, 20%, 30%, 40%, 50%, 60%, 70%, 80%, or 90% or more of the microorganism, if present in and/or on the target or the treated target composition, can be killed, destroyed, removed and/or inactivated by the present methods.

The present methods can be used to reduce population of any suitable microbe(s) in and/or on the target or the treated target composition by any suitable magnitude. In some embodiments, the present methods can be used to reduce a prokaryotic microbial population, e.g., a bacterial or an archaeal population. In other embodiments, the present methods can be used to reduce a eukaryotic microbial population, e.g., a protozoal or fungal population. In still other embodiments, the present methods can be used to reduce a viral population. Exemplary viral population can comprise a population of a DNA virus, a RNA virus, and a reverse transcribing virus.

The present methods can be used to stabilize or reduce a microbial population in and/or on the target or the treated target composition, wherein the target is an animal tissue and the contacting step minimizes or does not induce an organoleptic effect in and/or on the animal tissue and/or products of the same (e.g., milk). Typical organoleptic properties include the aspects of food or other substances as experienced by the senses, including taste, sight, smell, and touch, in cases where dryness and moisture are to be considered.

The present methods can be conducted at any suitable temperature range. In some embodiments, the present methods can be conducted at a temperature ranging from about 0° F. to about 120° F., for example about 0° F. to about 100° F., and/or about 32° F. to about 120° F.

In some embodiments, the present methods can comprise adding a peroxidase or a catalase to further reduce the hydrogen peroxide level in and/or on the target or the treated target composition. The peroxidase or catalase can be added in any suitable manner. In some embodiments, the peroxidase or catalase can be added to the target or the treated target composition before a composition used in the present methods is provided to the target. In other embodiments, the present compositions can be diluted into a suitable intermediate volume, and the peroxidase or catalase can be added to the diluted, intermediate volume. Thereafter, the diluted, intermediate volume, which contains the peroxidase or catalase, can be added to target. Any suitable peroxidase or catalase, including the ones described below, can be used in the present methods.

The compositions are suitable for antimicrobial efficacy against a broad spectrum of microorganisms, providing broad spectrum bactericidal and fungistatic activity. For example, the peracid biocides of this invention provide broad spectrum activity against wide range of different types of microorganisms (including both aerobic and anaerobic microorganisms), including bacteria, yeasts, molds, fungi, algae, and other problematic microorganisms associated with oil- and gas-field operations.

Exemplary microorganisms susceptible to the peracid compositions of the invention include, gram positive bacteria (e.g., *Staphylococcus aureus*, *Bacillus* species (sp.) like *Bacillus subtilis*, *Clostridia* sp.), gram negative bacteria (e.g., *Escherichia coli*, *Pseudomonas* sp., *Klebsiella pneumoniae*, *Legionella pneumophila*, *Enterobacter* sp., *Serratia* sp., *Desulfovibrio* sp., and *Desulfotomaculum* sp.), yeasts (e.g., *Saccharomyces cerevisiae* and *Candida albicans*), molds (e.g., *Aspergillus niger, Cephalosporium acremonium, Penicillium notatum*, and *Aureobasidium pullulans*), filamentous fungi (e.g., *Aspergillus niger* and *Cladosporium resinae*), algae (e.g., *Chlorella vulgaris, Euglena gracilis*, and *Selenastrum capricornutum*), and other analogous microorganisms and unicellular organisms (e.g., phytoplankton and protozoa). Other exemplary microorganisms susceptible to the peracid compositions of the invention include the exemplary microorganisms disclosed in U.S. patent application US 2010/0160449 A1, e.g., the sulfur- or sulfate-reducing bacteria, such as *Desulfovibrio* and *Desulfotomaculum* species.

In some embodiments, the composition used in the present methods may also contain a chelating agent for the purpose of removing ions from solution. The preferred embodiment of the invention uses 1-hydroxyethylidene-1,1-diphosphonic acid.

In some embodiments, differentiation of antimicrobial "-cidal" or "-static" activity, the definitions which describe the degree of efficacy, and the official laboratory protocols for measuring this efficacy are important considerations for understanding the relevance of antimicrobial agents in compositions. Antimicrobial compositions may affect two kinds of microbial cell damages. The first is a truly lethal, irreversible action resulting in complete microbial cell destruction or incapacitation. The second type of cell damage is reversible, such that if the organism is rendered free of the agent, it can again multiply. The former is termed bacteriocidal and the latter, bacteriostatic. A sanitizer and a disinfectant are, by definition, agents which provide antibacterial or bacteriocidal activity and may achieve at least a five-fold reduction (i.e., a five log 10 reduction) in microbial populations after a 30 second contact time (see AOAC method 960.09).

The diluted (or use) compositions may also be applied to soft surfaces such as skin (e.g., a hand). The diluted (or use) compositions may be employed as a foaming or non-foaming environmental sanitizer or disinfectant used on a skin surface, for example teats.

In other embodiments, the peroxyformic acid compositions of the present disclosure may be included in other products utilized on an animal tissue such as sterilants, sanitizers, disinfectants, preservatives, deodorizers, antiseptics, fungicides, germicides, sporicides, virucides, detergents, and bleaches. In still other embodiments, the peroxyformic acid compositions of the present disclosure may also be used in veterinary products such as mammalian skin treatments. The peroxyformic acid compositions may be employed in an antimicrobial foot bath for livestock or people.

In yet other embodiments, the present methods may be employed for reducing the population of pathogenic microorganisms, such as pathogens of humans, animals, and the like. Exemplary pathogenic microorganisms include fungi, molds, bacteria, spores, and viruses, for example, *S. aureus, E. coli, Streptococci, Legionella, Pseudomonas aeruginosa*, mycobacteria, tuberculosis, phages, or the like. Such pathogens may cause varieties of diseases and disorders, including Mastitis or other mammalian milking diseases, tuberculosis, and the like. The present methods may be used to reduce the population of microorganisms on skin or other external or mucosal surfaces of an animal. In addition, the present methods may be used to kill pathogenic microorganisms that spread through transfer by water, air, or a surface substrate. In some applications, the compositions of the present disclosure need only be applied to the skin, other external or mucosal surfaces of an animal.

In yet other embodiments, the present methods may also be employed by dipping a surface, including an animal tissue into the peroxyformic acid composition or solution of the present disclosure, soaking the tissue for a time sufficient to sanitize the equipment, and wiping or draining excess composition or solution off the tissue. The present methods may be further employed by spraying or wiping an animal tissue with the peroxyformic acid composition or solution, keeping the tissue wet for a time sufficient to sanitize the tissue, and removing excess composition or solution by wiping, draining vertically, vacuuming, etc.

The concentrations of peroxyformic acid and/or hydrogen peroxide in the peroxyformic acid compositions of the present disclosure can be monitored in any suitable manner. In some embodiments, the concentrations of peroxyformic acid and/or hydrogen peroxide in the peroxyformic acid and/or hydrogen peroxide compositions can be monitored using a kinetic assay procedure, e.g., the exemplary procedure disclosed in U.S. Pat. Nos. 8,017,409 and 8,236,573. This can be accomplished by exploiting the difference in reaction rates between peroxyformic acid and hydrogen peroxide when using, for example, a buffered iodide reagent to differentiate peroxyformic acid and hydrogen peroxide concentrations when both these analyte compounds are present in the use composition. The monitor may also determine the concentrations of peroxyformic acid and/or hydrogen peroxide in the presence of other additional ingredients, such as acidulants, one or more stabilizing agents, nonionic surfactants, semi-polar nonionic surfactants, anionic surfactants, amphoteric or ampholytic surfactants, adjuvants, solvents, additional antimicrobial agents or other ingredients which may be present in the use composition.

Methods for Treating a Biofilm

In yet another aspect, the present disclosure is directed to a method for treating a biofilm, which method comprises contacting a biofilm on an animal tissue, with an effective amount of peroxyformic acid for a sufficient time to stabilize, reduce and/or remove microbial population in and/or on said treated biofilm, or to stabilize, reduce and/or remove said biofilm on said surface.

The present methods can use any suitable concentration of peroxyformic acid. In some embodiments, the present methods can comprise contacting a biofilm on a surface with from about 10 ppm to about 500 ppm peroxyformic acid, e.g., 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, or 450-500 ppm peroxyformic acid.

The present methods can comprise contacting a biofilm on an animal tissue with an effective amount of peroxyformic acid for any suitable amount of time. In some embodiments, the present methods can comprise contacting a biofilm on an animal tissue with an effective amount of peroxyformic acid for from about 10 minutes to about 10 hours, e.g., about 10 minutes, 20 minutes, 30 minutes, 40 minutes, 50 minutes, 1 hour, 2 hours, 3 hours, 4 hours, 5 hours, 6 hours, 7 hours, 8 hours, 9 hours, or 10 hours. In an aspect, the contacting occurs for a period of time before degradation of the peroxyformic acid composition.

The present methods can be used to treat a biofilm made of or from any microbial population found on animal tissue, including, in particular a teat. In some embodiments, the present method can be used to treat a biofilm made of or from a prokaryotic microbial population, e.g., a bacterial or an archaeal population. Exemplary bacterial populations include a population of *Pseudomonas aeruginosa, Streptococcus mutans, Streptococcus pneumoniae*, a *Legionella* bacteria, or a *Bacillus* bacteria, e.g., *Bacillus* sp. Spore. In other embodiments, the present method can be used to treat a biofilm made of or from a eukaryotic microbial population, e.g., a protozoal or fungal population. In still other embodiments, the present method can be used to treat a biofilm made of or from a viral population.

The peroxyformic acid used in the present methods can be prepared using any suitable methods as disclosed herein according to the invention. In an embodiment, the peroxyformic acid used in the present methods can be prepared by contacting an ester of an alcohol and formic acid, with hydrogen peroxide or a substance that generates hydrogen peroxide when in contact with a liquid. For example, the peroxyformic acid used in the present methods can be prepared using any of the peroxyformic acid forming compositions described above or any of the methods described above. In other embodiments, the peroxyformic acid used in the present methods can be prepared in situ for the application of the formed peroxyformic acid.

Methods for Skin and Surface Sanitizing and Disinfecting

In yet another aspect, the various methods for treatment using the peroxyformic acid generated according to the methods of the invention can be employed for skin sanitizing and disinfectant, including for example methods for mastitis control. The rate of formation of the peroxyformic acid in situ is particularly beneficial for the application of use for skin disinfection. The disinfectant is generated in situ and provides on demand disinfectant. Beneficially, the applications of use employing the compositions for in situ generation of the disinfectant peroxyformic acid can provide glycerol as a leaving group which is further beneficial to the skin treated with the disinfectant composition. Without being limited to a particular mechanism of action and/or benefit, the glycerol provides an emmollient to the treated skin surface. In an embodiment, the surface, including skin or other external or mucosal surfaces of an animal in need of disinfectant is contacted with an effective amount of peroxyformic acid for a sufficient time to reduce and/or remove microbial population on said treated surface.

The present methods can use any suitable concentration of peroxyformic acid for disinfecting skin by applying a liquid, namely a solution, to the skin surface. In some embodiments, the present methods can comprise contacting a surface with from about 10 ppm to about 500 ppm peroxyformic acid, e.g., 10-20 ppm, 20-30 ppm, 30-40 ppm, 40-50 ppm, 50-60 ppm, 60-70 ppm, 70-80 ppm, 80-90 ppm, 90-100 ppm, 100-150 ppm, 150-200 ppm, 200-250 ppm, 250-300 ppm, 300-350 ppm, 350-400 ppm, 400-450 ppm, 450-500 ppm peroxyformic acid. In a preferred aspect, the methods of contacting provide from about 10 ppm to about 500 ppm peroxyformic acid for disinfectant generated in situ within a matter of minutes.

The present methods can comprise contacting a surface with an effective amount of peroxyformic acid for any suitable amount of time. In some embodiments, the present methods can comprise contacting a surface with an effective amount of peroxyformic acid for from about 10 minutes to about an hour The present methods can be used to treat a surface, including skin, having a contaminated surface from any suitable microbial populations. In some embodiments, the present method can be used to treat a surface made of or from a prokaryotic microbial population, e.g., a bacterial or an archaeal population. Exemplary bacterial populations include a population of Staphylococcus aureus, Streptococcus agalactiae, Streptococcus dysagalactiae, and Streptococcus uberis. The methods are suitable for disinfecting common mastitis causing pathogens, including both contagious and environmental pathogens. Contagious bacteria, such as Streptococcus agalactiae and Staphylococcus aureus, primarily colonize host tissue sites such as mammary glands, teat canals, teat skin lesions etc. and are spread from one infected bovine to another during the milking process. Environmental bacteria, often streptococci, enterococci and coliform organisms, are commonly present within the bovine's surroundings from sources such as bovine feces, soil, plant material, bedding or water, and infect by casual opportunistic contact with an animal during the inter-milking period.

The methods of disinfecting a skin surface may include the contacting of a surface with an effective amount of the disinfecting composition by various routes of application. In an aspect, the disinfectant composition can contact the surface by dipping the skin surface (such as teats) in solution, spray applying the solution to the surface, or by dipping in a foam produced from the solution. In a preferred aspect, a method of treating teats of lactating animals comprises applying an effective amount of the composition by dipping the teats in solution, spray applying the solution to teats, or by dipping in a foam produced from the solution.

The peroxyformic acid used in the present methods can be prepared using any suitable methods disclosed herein. In some embodiments, the peroxyformic acid used in the present methods can be prepared by contacting an ester of an alcohol and formic acid, with hydrogen peroxide or a substance that generates hydrogen peroxide when in contact with a liquid. For example, the peroxyformic acid used in the present methods can be prepared using any of the peroxyformic acid forming compositions described above or any of the methods described above. In other embodiments, the peroxyformic acid used in the present methods can be prepared in situ for the application of the formed peroxyformic acid.

In some embodiments, the present methods can further comprise contacting the surface with a polyol, including a skin conditioning polyol, or other emollient and/or humectant. In an aspect, an emollient and/or humectant is formulated with the disinfectant to lubricate, condition and generally reduce and promote the healing of irritation on the surface of application which may result either from the disinfectant agent, from mechanical action employed or from environmental conditions such as wind chill, dehydration, abrasion and sunburn. Any water soluble or dispersible skin conditioning agent may be used in this present disclosure. Compositions such as esters of alcohols are useful in the invention including glycerin, sorbitol, mannitol, and propylene and ethylene glycol and their homopolymers, as well as ethyl, methyl, propyl, butyl, pentyl, heptyl and benzyl alcohols; fatty acid esters of simple monohydril alcohols including isopropyl palmitate or isopropyl myristate and similar esters; polyol esters of fatty acids; and, ethoxylated lanolins, vegetable oils, and similar natural sourced derivatives such as aloe. Preferred emollients to be used in the invention include glycerin, glycerol, propylene glycol, dipropylene glycol, sorbitol, aloe, shea butter, coco butter, allantoin, or a mixture thereof.

In a preferred aspect, monohydric alcohols include ethanol, methanol, propanol, butanol, pentanol, heptanol, and benzyl alcohol. In an additional aspect, polyols include glycerin, propylene glycol, sorbitol, polyglycerol, and mixtures thereof. In a preferred aspect, the surface is contacted with a disinfectant liquid, including a solution comprising the peroxyformic acid and the polyol in an amount from about 0.5 wt-% to about 50 wt-% of the disinfectant liquid. In a preferred aspect, the surface is contacted with a disinfectant liquid, including a solution comprising the peroxyformic acid and the polyol in an amount from about 1 wt-% to about 10 wt-% of the disinfectant liquid.

In some embodiments, the present methods can further comprise contacting the surface with the peroxyformic acid and a $C_2$-$C_{22}$ percarboxylic acid. Exemplary $C_2$-$C_{22}$ percarboxylic acids include peroxyacetic acid, peroxyoctanoic acid and/or peroxysulfonated oleic acid. In other embodiments, the present methods can further comprise contacting the surface with a surfactant. Exemplary surfactants include an anionic surfactant, a nonionic surfactant, a cationic surfactant as well as an amphoteric surfactant. In still other embodiments, the present methods can further comprise contacting the surface with a solvent. Exemplary solvents include an alcohol, an ester, a glycol ether, an amide, a hydrocarbon etc. In still other embodiments, the present methods can further comprise contacting the surface with an enzyme.

In some embodiments, the present methods can further comprise contacting the surface with the peroxyformic acid composition further comprising surface wetting agents. The surfactant or surfactant admixture of the present disclosure can be selected from compatible water soluble or water dispersible nonionic, or anionic surface-active agents; or mixtures of each or both types. Nonionic and anionic surfactants offer diverse and comprehensive commercial selection, low price; and, most important, excellent detersive effect—meaning surface wetting. Surface—active or "wetting agents" function to increase the penetrant activity of the invention into the tissue surface at risk from mastitis causing pathogens. Nonionic surfactants useful in the invention are generally characterized by the presence of an organic hydrophobic group and an organic hydrophilic group and are typically produced by the condensation of an organic aliphatic, alkyl aromatic or polyoxyalkylene hydrophobic compound with a hydrophilic alkaline oxide moiety which in common practice is ethylene oxide or a polyhydration product thereof, polyethylene glycol. Practically any hydrophobic compound having a hydroxyl, carboxyl, amino, or amido group with a reactive hydrogen atom can be condensed with ethylene oxide, or its polydration adducts, or its mixtures with alkoxylenes such as propylene oxide to form a nonionic surface-active agent. The length of the hydrophilic polyoxyalkylene moiety which is condensed with any particular hydrophobic compound can be readily adjusted to yield a water dispersible or water soluble compound having the desired degree of balance between hydrophilic and hydrophobic properties.

Also useful in the present disclosure are surface active substances which are categorized as anionics because the charge on the hydrophobe is negative; or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Of the cations (counterions) associated with these polar groups, sodium, lithium and potassium impart water solubility and are most preferred in compositions of the present disclosure. Examples of suitable synthetic, water soluble anionic compounds are the alkali metal (such as sodium, lithium and potassium) salts or the alkyl mononuclear aromatic sulfonates such as the alkyl benzene sulfonates containing from about 5 to about 18 carbon atoms in the alkyl group in a straight or branched chain, e.g., the salts of alkyl benzene sulfonates or of alkyl naphthalene sulfonate, dialkyl naphthalene sulfonate and alkoxylated derivatives. Other anionic detergents are the olefin sulfonates, including long chain alkene sulfonates, long chain hydroxyalkane sulfonates or mixtures of alkene-sulfonates and hydroxyalkanae-sulfonates and alkylpoly (ethyleneoxy) ether sulfonates. Also included are the alkyl sulfates, alkyl poly (ethyleneoxy) ether sulfates and aromatic poly (ethyleneoxy) sulfates such as the sulfates or condensation products of ethylene oxide and nonyl phenol (usually having 1 to 6 oxyethylene groups per molecule).

In an aspect, oxidatively susceptible or acid hydrolytically susceptible surfactants are employed as wetting agents. Exemplary oxidatively susceptible surfactants comprise polyethylene glycol based surfactant, polyglycerol, polyol sugar based surfactants, and mixtures thereof. Exemplary surfactants include, alcohol ethoxylates, EO/PO copolymers exemplified by poloxamers, glycerol and polyglycerol ester surfactants, polysorbate surfactants exemplified by Tween® surfactants, and sugar based surfactants exemplified by alkyl polyglucosides such as Glucopon® surfactants. Additional disclosure of suitable wetting agents is set forth in U.S. Pat. No. 6,749,869 and Reissue No. RE41279E, each of which are herein incorporated by reference in their entirety. Beneficially, the disinfectant compositions are stable with peroxyformic acid compositions generated in situ, unlike conventional food based or skin friendly surfactants which are not stable in highly oxidative or very low pH environments of traditional equilibrium or concentrate peracids.

In some embodiments, the present methods can further comprise contacting the surface with the peroxyformic acid composition further comprising a dye or colorant. In an aspect, the peroxyformic acid of the disinfectant composition is provided with a dye or colorant to provide a mechanism for color marking of the disinfectant composition. Beneficially, the peroxyformic acid generated in situ does not have shelf-stability and formulation incompatibility with traditional colorants, as is experienced with traditional equilibrium and concentrate peracid systems. In an aspect, the dye or colorant is a food and/or drug additive dye. In an aspect, the dye or colorant is not a color changing or indicator system. In an aspect, complexed iodines offer the advantage of being chromophoric, i.e. easily visible when applied onto the skin. Other antimicrobial agents do not have this feature; therefore, compositions of this invention may include a water soluble or dispersible coloring agent (dye or pigment or mixtures) which renders the composition chromophoric, having sharp contrast to teat skin and permitting the dairy herd manager to visually discern that the teats have been treated.

In further aspects, the disinfectant compositions may be comprised of any number of optional ingredients. Generally, in accordance with the invention, there may be included within this composition formulary adjuvants which assist in the application of the invention with respect to physical and chemical stability, barrier film formation, skin or teat health maintenance, performance, physical form and manufacturing process anesthetics. Of course, these functions may be accomplished exclusively by composition ingredients already described or admixtures thereof however, formulary or application or performance situations may occur requiring additional effect which may be accomplished by introducing an additional inorganic or organic agent or agents and mixtures thereof into the composition.

The compositions of the invention may optionally include medicaments, for example sunscreens such as paraamino benzoic acid and healing agents such as allantoin or urea to provide curative action and stimulation of formation of new tissue; preservatives such as methyl paraben, propyl paraben, sorbic and benzoic acids or salts thereof to retard bacterial growth and prolong shelf life; antioxidants such as BHT (butylated hydroxytoluene), BHA (butylated hydroxyanisole), TBHQ (tert-butylhydroquinone), or propyl gallate to retard oxidative or hydrolytic degradation; sequestering agents such as aminopolyacetates, polyphosphonates, aminpolyphosphonates, polycarboxylates, and condensed phosphates; dispersants or suspending agents having polyelectrolytic character such as polyacrylate and similar polycarboxylates of homopolymeric or copolymeric structure; and manufacturing processing agents, for example defoam additives employed to facilitate blending and mixing.

A wide variety of ingredients useful in skin disinfection, including mastitis control, treatment can be included in the compositions hereof. This list is not intended to be exhaustive and other optional ingredients, which may not be listed, but which are well known in the art, may also be utilized in the composition. The examples are not intended to be limited in any way. In certain cases, some of the individual adjuvants may overlap other categories. The adjuvants employed will be selected so as not to interfere with the antimicrobial action of the composition and to avoid physical or chemical instability of the product.

The present methods can be conducted at any suitable temperature ranges as disclosed herein. In general, the pH of bovine mastitis control treatments can vary from a low of about pH 2.0 to a maximum of approximately 8 depending primarily upon the choice of antimicrobial agent being incorporated in the composition because optimal efficacy normally occurs with a specific, narrow, pH range. Therefore, the buffering agent or system is chosen accordingly. The present methods are preferably conducted at a slightly alkaline pH, or a near neutral pH of the peroxyformic acid compositions. In some embodiments, the pH is from about 2-8, 3-8, and preferably 4-7.

Beneficially, the methods of disinfection are suitable for in situ generation of the peroxyformic acid under conditions suitable for the disinfection. In an aspect, the peroxyformic acid is generated and used within a matter of minutes at a point of use. In an aspect, at least about 1 ppm peroxyformic is generated within about 10 minutes of contacting the hydrogen peroxide or hydrogen peroxide forming compound and the ester of an alcohol and formic acid. In an aspect, at least about 100 ppm or at least about 500 ppm peroxyformic is generated within about 10 minutes of contacting the hydrogen peroxide or hydrogen peroxide forming compound and the ester of an alcohol and formic acid.

In further aspects, the present peroxyformic acid forming compositions can be configured to form a liquid, e.g., a solution, that comprises any suitable concentration of peroxyformic acid within any suitable time. For example, the hydrogen peroxide or hydrogen peroxide forming compound and the ester of an alcohol and formic acid in the present peroxyformic acid forming compositions can be configured to be contacted with each other to form a liquid and/or solid, e.g., a solution, that comprises any suitable concentration of peroxyformic acid within any suitable time.

In a preferred embodiment, a method of cleaning a teat, a compositions can be employed pre-milking to clean the teat, wherein that composition does not contain a dye, and a composition can be employed post-milking that does contain a dye.

EXAMPLES

Embodiments of the present disclosure are further defined in the following non-limiting Examples. It should be understood that these Examples, while indicating certain embodiments, are given by way of illustration only. From the above discussion and these Examples, one skilled in the art can ascertain the essential characteristics of the compositions and methods, and without departing from the spirit and scope thereof, can make various changes and modifications to adapt it to various usages and conditions. Thus, various modifications of the embodiments, in addition to those shown and described herein, will be apparent to those skilled in the art from the foregoing description. Such modifications are also intended to fall within the scope of the appended claims.

Example 1. Generation of Performic Acid from Hydrogen Peroxide Premix

Glycerol formates were added to hydrogen peroxide premixes as illustrated by Table 1, to generate performic acid according to the compositions of Table 2. The concentrations of performic acid that were generated were measured by an iodometric titration method. The conditions for generating peroxyformic acid and the results of the generation process are summarized in FIG. 1.

TABLE 1

Hydrogen Peroxide Premix Compositions for Use in Generating PFA

| Component | Amount (g) | Wt. % |
|---|---|---|
| Hydrogen Peroxide (50%) | 0.80 | 0.80 |
| pH Buffer | 0.059 | 0.059 |
| Alkalinity Source | 0.0238 | 0.0238 |
| Diphosphonic Acid | 0.059 | 0.059 |
| DI Water | 97.003 | 97.03 |
| Total | 100.00 | 100.00 |

TABLE 2

Composition of Performic Acid (PFA) Generation

| Component | Amount (g) | Wt. % |
|---|---|---|
| Glycerol formates | 1.5 | 3.0 |
| Hydrogen Peroxide Premix of Table 1 | 48.5 | 97.0 |
| Total | 50.0 | 100.0 |

Example 2. Conditions for Generating Performic Acid from a Hydrogen Peroxide Premix To evaluate the conditions of generation, glycerol formates were added to hydrogen peroxide premix to generate performic acid. The hydrogen peroxide premix was prepared according to Table 3, and combined with glycerol formates according to Table 4. The concentrations of performic acid that were generated were measured by an iodometric titration method. The conditions for generating peroxyformic acid and the results of the generation process are summarized in Table 5.

TABLE 3

Hydrogen Peroxide Premix Compositions for Use in Generating PFA

| Component | Amount (g) | Wt. % |
|---|---|---|
| Hydrogen Peroxide (50%) | 2.0 | 2.0 |
| pH Buffer | 0.118 | 0.118 |
| Alkalinity Source | 0.004 | 0.004 |
| DI Water | 97.88 | 97.88 |
| Total | 100.00 | 100.00 |

TABLE 4

Composition of Performic Acid (PFA) Generation

| Component | Amount (g) | Wt. % |
|---|---|---|
| Glycerol formates | 2.0 | 2.0 |
| Hydrogen Peroxide Premix of Table 1 | 98.0 | 98.0 |
| Total | 100.0 | 100.0 |

TABLE 5

Conditions for Generation of Performic Acid (PFA)

| Composition | Active Ingredients | Minimum PFA (ppm) | Time to reach the minimum PFA | Duration of minimum PFA |
|---|---|---|---|---|
| A | 2% $H_2O_2$, 2% glycerol formates | 200 | 10 min. | 24 hr. |
| B | 2% $H_2O_2$, 3% glycerol formates | 300 | 10 min. | 24 hr. |
| C | 0.8% $H_2O_2$, 3% glycerol formates | 100 | 10 min. | 24 hr. |
| D | 0.4% $H_2O_2$, 3% glycerol formates | 75 | 10 min. | 24 hr. |

Example 3. Stability of Hydrogen Peroxide Premix

Figure 2:
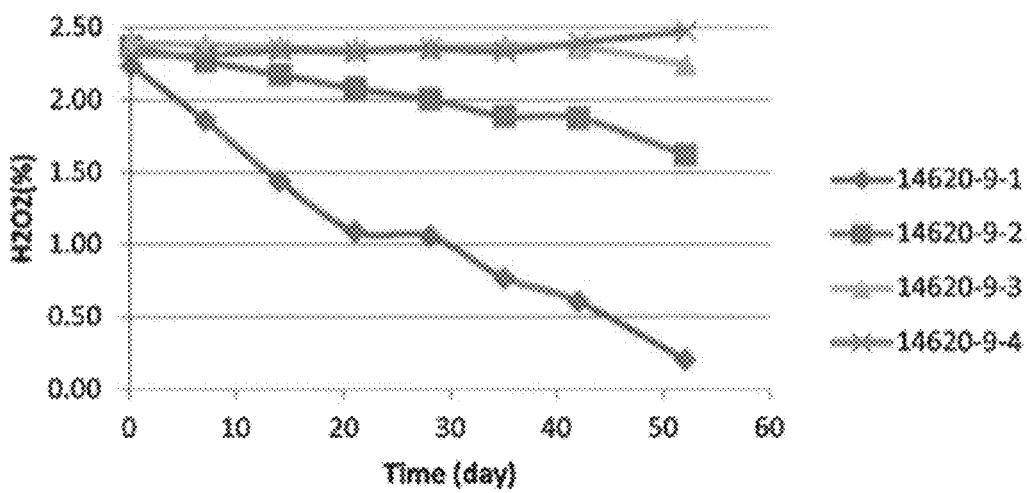
FIG. 2 illustrates the accelerated stability of hydrogen peroxide premixes according to embodiments of the present application.

The accelerated stability of a hydrogen peroxide premix composition comprising hydrogen peroxide, a pH adjustment reagent, and stabilizers were assessed by preparing the hydrogen peroxide premixes according to Table 6 and storing the premix in a 40° C. oven over approximately 7.5 weeks. The stability, as evaluated by the presence of hydrogen peroxide, is depicted in Table 7 and FIG. 2, where the diamond data points correspond to formulation 1 (the control having no stabilizer), the square data points correspond to formulation 2, the triangle data points correspond to formulation 3, and the X-shaped data points correspond to formulation 4 as described in Table 6.

TABLE 6

Compositions of Hydrogen Peroxide Premixes

| Sample | Form. 1 | Form. 2 | Form. 3 | Form. 4 |
|---|---|---|---|---|
| Hydrogen Peroxide (50%) (wt. %) | 10 | 10 | 10 | 10 |
| Humectant (wt. %) | 10 | 10 | 10 | 10 |
| pH Buffer (wt. %) | 6.8 | 6.8 | 6.8 | 6.8 |
| Pyridine carboxylic acid (wt. %) | 0.0 | 0.1 | 0.0 | 0.0 |
| Diphosphonic Acid (wt. %) | 0.0 | 0.0 | 0.2 | 0.0 |
| Phosphonic Acid (wt. %) | 0.0 | 0.0 | 0.0 | 0.2 |
| DI Water (g) | 200 | 200 | 200 | 200 |
| pH adjusted to: | 5.30 | 5.30 | 5.30 | 5.29 |

TABLE 7

Accelerated Stability of Hydrogen Peroxide Premixes Under 40° C.

| Storage Time (Days) Under 40° C. | Form. 1 | Form. 2 | Form. 3 | Form. 4 |
|---|---|---|---|---|
| 0 | 2.24 | 2.37 | 2.40 | 2.32 |
| 7 | 1.86 | 2.27 | 2.38 | 2.31 |
| 14 | 1.44 | 2.17 | 2.36 | 2.34 |
| 21 | 1.09 | 2.08 | 2.35 | 2.33 |
| 28 | 1.06 | 2.00 | 2.36 | 2.36 |
| 35 | 0.77 | 1.89 | 2.37 | 2.34 |
| 42 | 0.61 | 1.88 | 2.36 | 2.40 |
| 52 | 0.21 | 1.62 | 2.25 | 2.47 |

Example 4. Stability of Hydrogen Peroxide Premix with Self-Indicators

The accelerated stability of a hydrogen peroxide premix composition comprising hydrogen peroxide, a pH adjustment reagent, stabilizers, and dyes utilized for self-indication were assessed by preparing the hydrogen peroxide premixes according to Table 8 and storing the premix in a 40° C. oven over 13-15 weeks. The stability, as evaluated by the presence of hydrogen peroxide, is depicted in Table 9.

TABLE 8

Compositions of Hydrogen Peroxide Premixes with Dyes

| Sample | Form. 1 | Form. 2 |
|---|---|---|
| Hydrogen Peroxide (50%) (wt. %) | 4.00 | 16.00 |
| Humectant (wt. %) | 5.00 | 20.00 |
| Alkyl esters (wt. %) | 3.00 | 12.00 |
| FD&C Yellow 5 (wt. %) | 0.30 | 1.20 |
| Diphosphonic Acid (wt. %) | 0.33 | 1.32 |
| pH Buffer (wt. %) | 0.18 | 0.70 |

TABLE 8-continued

Compositions of Hydrogen Peroxide Premixes with Dyes

| Sample | Form. 1 | Form. 2 |
|---|---|---|
| Alkalinity Source | 0.068 | 0.27 |
| DI Water (g) | 87.12 | 48.51 |
| pH adjusted to: | 4.75 | 4.78 |

TABLE 9

Accelerated Stability of Hydrogen Peroxide Premixes with Dyes Under 40° C.

| Storage Time (Days) Under 40° C. | Form. 1 | Form. 2 |
|---|---|---|
| 0 | 2.10 | 8.02 |
| 7 | 2.02 | 7.92 |
| 14 | 2.05 | 7.84 |
| 21 | 2.04 | n/a |
| 28 | n/a | 7.67 |
| 32 | n/a | n/a |
| 35 | 2.02 | n/a |
| 42 | n/a | 7.48 |
| 55 | n/a | 7.33 |
| 49 | 2.06 | n/a |
| 63 | 2.09 | n/a |
| 95 | n/a | 6.96 |
| 103 | 2.16 | n/a |

It was surprisingly found that with the inclusion of stabilizer, the FD&C dyes are stable in the hydrogen peroxides premixes.

Example 5. Comparison of Self-Indicators in Hydrogen Peroxide Premix

The hydrogen peroxide premixes were prepared according to Table 10 with differing types of FD&C dyes. The compositions were stored in a 40° C. oven for approximately 13 weeks. Their stability, as evaluated by the presence of hydrogen peroxide, was compared and is depicted in Table 11.

TABLE 10

Compositions of Hydrogen Peroxide Premixes with Different Self-Indicators

| Sample | Form. 1 | Form. 2 |
|---|---|---|
| Hydrogen Peroxide (50%) (wt. %) | 10.00 | 10.00 |
| Humectant (wt. %) | 50.00 | 50.00 |
| First Alkyl ester (wt. %) | 1.50 | 1.50 |
| Second Alkyl ester (wt. %) | 1.50 | 1.50 |
| FD&C Yellow 5 (wt. %) | 1.50 | 0.00 |
| FD&C Yellow 6 (wt. %) | 0.00 | 1.50 |
| Diphosphonic Acid (wt. %) | 0.33 | 0.33 |
| DI Water (wt. %) | 35.17 | 35.17 |

TABLE 11

Accelerated Stability of Hydrogen Peroxide
Premixes with Different Self-Indicators Under 40° C.

| Compositions | Form. 1 | | Form. 2 | |
|---|---|---|---|---|
| Storage Time (Days) Under 40° C. | H$_2$O$_2$ (wt. %) | $\lambda_{423\,nm}$ (0.1% solution) | H$_2$O$_2$ (wt. %) | $\lambda_{423\,nm}$ (0.1% solution) |
| 0 | 4.85 | 0.840 | 4.98 | 0.876 |
| 30 | 4.96 | 0.777 | 5.02 | 0.873 |
| 60 | 5.01 | 0.601 | 5.06 | 0.805 |
| 90 | 5.07 | 0.555 | 5.01 | 0.795 |

All the FD&C dyes were stable in the hydrogen peroxide premixes. However, surprisingly, while structurally similar, FD&C yellow 6 is significantly more stable than FD&C yellow 5 under the tested conditions.

Figure 3:
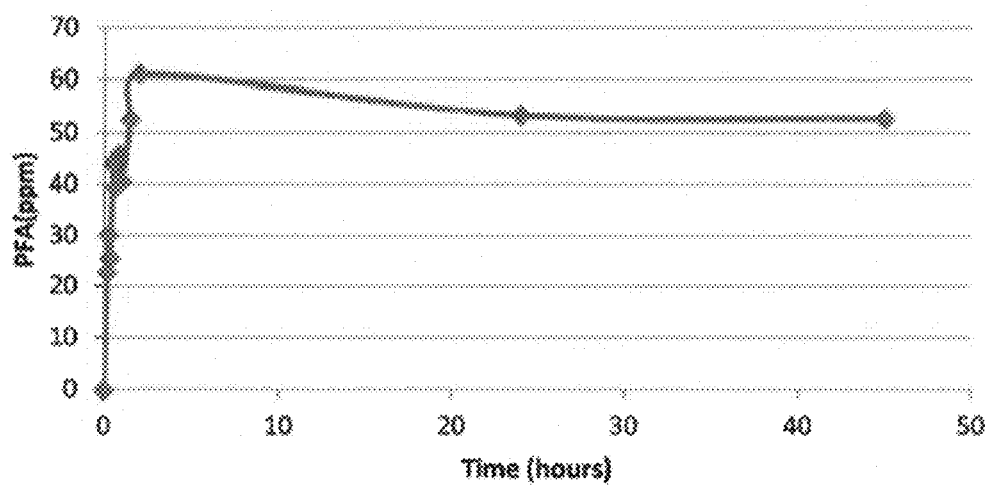
FIG. 3 illustrates the generation of peroxyformic acid by a combination of ethyl formates with hydrogen peroxide premixes according to embodiments of the present application.

Example 6. Generation of Performic Acid from Ethyl Formates Under Ambient Conditions Ethyl formates were added to hydrogen peroxide to generate performic acid under ambient conditions. The concentrations of performic acid that were generated were measured by an iodometric titration method. The amount of formic acid generated is depicted in Table 12, and the rate of generation is shown in FIG. 3.

TABLE 12

Generation of Performic Acid from Ethyl Formates

| Time (hr) | Sample Wt. (g) | V$_{0.1N\,Na2SO3}$ (ml) | PFA (ppm) |
|---|---|---|---|
| 0 | n/a | n/a | 0 |
| 0.17 | 2.73 | 0.02 | 22.7 |
| 0.25 | 4.09 | 0.04 | 30.3 |
| 0.33 | 3.61 | 0.03 | 25.8 |
| 0.50 | 4.21 | 0.06 | 44.2 |
| 0.67 | 3.13 | 0.04 | 39.6 |
| 0.83 | 3.38 | 0.05 | 45.9 |
| 1.0 | 3.04 | 0.04 | 40.8 |
| 1.50 | 2.94 | 0.05 | 52.7 |
| 2.00 | 3.04 | 0.06 | 61.2 |
| 24.0 | 3.48 | 0.06 | 53.4 |
| 45.0 | 3.52 | 0.06 | 52.8 |

Example 7. Generation of Performic Acid from Ethyl Formates Under Ambient Conditions For treatment of an animal tissue, particularly dairy cattle, it is important that a treatment solution maintain biocidal efficacy in the presence of milk. The treatment compositions of the present comprising 100 ppm were evaluated against both gram negative and gram positive microorganisms (*S. aureus* and *E. coli*) in the presence of 10% milk with 15 seconds of contact time. The evaluation was conducted at both room temperature and at 4° C. For comparison, the most commonly used teat dip actives, iodine-based teat dips, were also tested under the same conditions.

Figure 4:
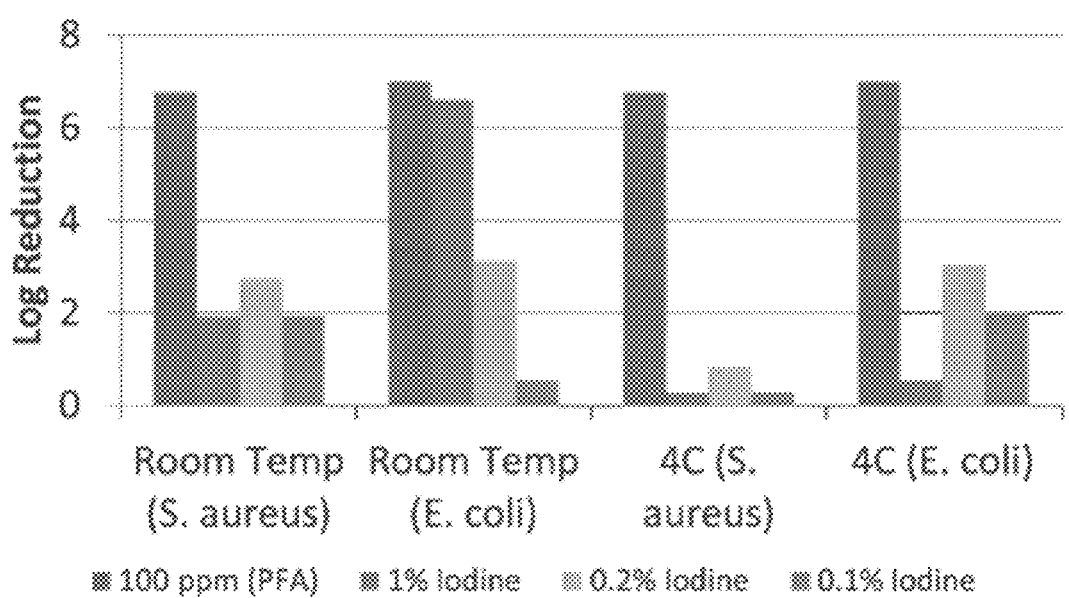
FIG. 4 illustrates the biocidal efficacy of the treatment compositions of the present application in the presence of milk.

The results of this evaluation are summarized in FIG. 4. FIG. 4 demonstrates that the compositions of the present application using performic acid provided substantially improved log reduction against both gram positive and gram negative microorganisms under a variety of testing conditions.

Example 8. Skin Compatibility Evaluation

For treatment of an animal tissue, particularly dairy cattle, it is important that a treatment solution be mild on skin under the application conditions. The treatment compositions of the present application were evaluated on bovine teats over the course of four weeks. The compositions were applied on the teats twice daily. If the teats showed no difference from the control teats, then it was scored as skin compatible. The results are summarized in Table 13.

TABLE 13

Skin Compatibility

| | Ingredients | | | | |
|---|---|---|---|---|---|
| Trial | H$_2$O$_2$ | Glycerol Formates | Glycerin | PFA (ppm) | Skin Compatibility |
| 1 | 2.0% | 2.0% | 5.0% | 300 | 0% |
| 2 | 0.8% | 3.0% | 5.0% | 100 | 70% |
| 3 | 0.8% | 3.0% | 10.0% | 100 | 90% |
| 4 | 0.4% | 3.0% | 7.0% | 75 | 100% |

The results show that the treatment compositions of the present application provide improved skin compatibility on bovine teats.

The detailed description set-forth above is provided to aid those skilled in the art in practicing the present disclosure. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

The claimed invention is:

1. A method of preventing and/or treating mastitis comprising:
   applying an antimicrobial teat dip composition to an animal tissue; wherein the antimicrobial teat dip composition comprises
   hydrogen peroxide or a hydrogen peroxide forming compound;
   an ester of an alcohol and formic acid;
   a dye, wherein the dye is red #40, yellow #5, yellow #6, or a mixture thereof; and
   water; and
   wherein the pH of the antimicrobial teat dip composition is between about 2 and about 7;
   wherein the dye results in the coloring of a teat without interfering with the antimicrobial function of the composition; and
   removing the antimicrobial teat dip composition from the animal tissue.

2. The method of claim 1, wherein the ester of an alcohol and formic acid comprises a glycerol formate, an ethylene glycol formate, a pentaerythritol formate, a mannitol formate, a propylene glycol formate, a sorbitol formate, a sugar formate, a methyl formate, an ethyl formate, a propyl formate, a butyl formate, a heptyl formate, a pentyl formate, a benzyl formate, or a mixture thereof.

3. The method of claim 2, wherein the sugar formate is a glycerol formate, a sucrose formate, a dextrin formate, a maltodextrin formate, a starch formate, or a mixture thereof.

4. The method of claim 1, wherein the antimicrobial teat dip composition provides a 4-log reduction in *Staphylococcus aureus* and *Escherichia coli*.

5. The method of claim 1, further comprising an emollient, a medicament, a foaming surfactant, a buffering agent, a stabilizing agent, or a combination thereof.

6. The method of claim 5, wherein the emollient comprises glycerin, glycerol, propylene glycol, dipropylene glycol, sorbitol, aloe, shea butter, coco butter, allantoin, or a mixture thereof; wherein the stabilizing agent comprises a phosphonate, a dicarboxylic acid, a pyridine carboxylic acid, or a mixture thereof; wherein the buffering agent comprises succinic acid or a salt thereof; and wherein the foaming surfactant is polysorbate and/or dioctyl sulfosuccinate sodium salt.

7. The method of claim 5, wherein the medicament comprises paraamino benzoic acid, allantoin, urea, or a mixture thereof.

8. The method of claim 1, wherein the composition comprises between about 90.0 wt. % and about 99.9 wt. % water, between about 50 ppm and about 2 wt. % of hydrogen peroxide or a hydrogen peroxide forming compound, between about 50 ppm and about 350 ppm of performic acid; and wherein the composition is stable for at least 24 hours.

9. The method of claim 1, wherein the animal tissue is a bovine teat.

10. A method of preventing and/or treating mastitis comprising:
   diluting an antimicrobial teat dip composition to form a ready-to-use teat dip composition;
      wherein the antimicrobial teat dip composition comprises
      hydrogen peroxide or a hydrogen peroxide forming compound;
      an ester of an alcohol and formic acid;
      a dye, wherein the dye is red #40, yellow #5, yellow #6, or a mixture thereof; and
      water; and
      wherein the pH of the antimicrobial teat dip composition is between about 2 and about 7;
   applying the ready-to-use teat dip composition to an animal tissue; wherein the dye results in the coloring of a teat without interfering with the antimicrobial function of the composition; and
   removing the ready-to-use teat dip composition from the animal tissue.

11. The method of claim 10, wherein the ester of an alcohol and formic acid comprises a glycerol formate, an ethylene glycol formate, a pentaerythritol formate, a mannitol formate, a propylene glycol formate, a sorbitol formate, a sugar formate, a methyl formate, an ethyl formate, a propyl formate, a butyl formate, a heptyl formate, a pentyl formate, a benzyl formate, or a mixture thereof.

12. The method of claim 11, wherein the sugar formate is a glycerol formate, a sucrose formate, a dextrin formate, a maltodextrin formate, a starch formate, or a mixture thereof.

13. The method of claim 10, wherein the antimicrobial teat dip composition provides a 4-log reduction in *Staphylococcus aureus* and *Escherichia coli*.

14. The method of claim 10, further comprising an emollient, a medicament, a foaming surfactant, a buffering agent, a stabilizing agent, or a combination thereof.

15. The method of claim 14, wherein the emollient comprises glycerin, glycerol, propylene glycol, dipropylene glycol, sorbitol, aloe, shea butter, coco butter, allantoin, or a mixture thereof; wherein the stabilizing agent comprises a phosphonate, a dicarboxylic acid, a pyridine carboxylic acid, or a mixture thereof; wherein the buffering agent comprises succinic acid or a salt thereof; and wherein the foaming surfactant is polysorbate and/or dioctyl sulfosuccinate sodium salt.

16. The method of claim 14, wherein the medicament comprises paraamino benzoic acid, allantoin, urea, or a mixture thereof.

17. The method of claim 10, wherein the animal tissue is a bovine teat.

18. The method of claim 10, wherein the antimicrobial teat dip composition comprises between about 50 wt. % and about 99 wt. % water, and between about 0.1 wt. % and about 20 wt. % of hydrogen peroxide or a hydrogen peroxide forming compound.

19. The method of claim 10, wherein the ready-to-use teat dip composition comprises between about 90.0 wt. % and about 99.9 wt. % water, between about 50 ppm and about 2 wt. % of hydrogen peroxide or a hydrogen peroxide forming compound, between about 50 ppm and about 350 ppm of performic acid; and wherein the composition is stable for at least 24 hours.

20. The method of claim 10, further comprising the step of combining a first premix and a second premix to form the antimicrobial teat dip composition; wherein the first premix comprises the ester of the alcohol and formic acid; wherein the second premix comprises the hydrogen peroxide or the hydrogen peroxide forming compound and the dye.

21. The method of claim 1, wherein the antimicrobial teat dip composition is removed from the animal tissue after at least 1 minute of contact.

22. The method of claim 10, wherein the ready-to-use teat dip composition is removed from the animal tissue after at least 1 minute of contact.

* * * * *